United States Patent [19]
Yoshioka et al.

[11] Patent Number: 4,812,563
[45] Date of Patent: Mar. 14, 1989

[54] 6-(DISUBSTITUTED AMINO)CARBAPENAM COMPOUNDS

[75] Inventors: Takeo Yoshioka, Ayase; Noritaka Chida, Sagamihara; Azuma Watanabe, Yokohama; Yasuo Fukagawa, Kamakura; Tomoyuki Ishikura, Chigasaki, all of Japan

[73] Assignee: Sanraku Incorporated, Tokyo, Japan

[21] Appl. No.: 24,160

[22] Filed: Mar. 10, 1987

[30] Foreign Application Priority Data

Mar. 11, 1986 [JP] Japan ................... 61-51556

[51] Int. Cl.⁴ ......................................... C07D 487/04
[52] U.S. Cl. ................................................. 540/302
[58] Field of Search ........................................ 540/302

[56] References Cited

U.S. PATENT DOCUMENTS 4,298,741 11/1981 Christensen ..................... 546/272
4,576,746 3/1986 Favara et al. ..................... 260/239

FOREIGN PATENT DOCUMENTS 0163452 12/1985 European Pat. Off. .

Primary Examiner—Robert Gerstl
Attorney, Agent, or Firm—Wenderoth, Lind & Ponack

[57] ABSTRACT

A compound represented by the formula

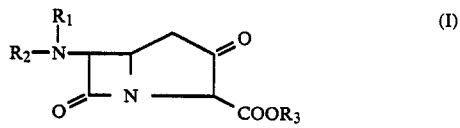

wherein $R_1$ represents a lower alkyl group or a lower haloalkyl group; $R_2$ represents a lower alkyl group, a lower haloalkyl group, an aralkyl group, or a group of the formula —$COOR_4$ or —$SO_2R_5$ in which $R_4$ represents an alkyl group or a substituted or unsubstituted aralkyl group and $R_5$ represents an alkyl group or a substituted or unsubstituted aryl group; and $R_3$ represents a hydrogen atom or a carboxyl protecting group which can be easily split off. This compound is useful in the production of a 6-(disubstituted amino)carbapenem-series antibiotic.

1 Claim, 1 Drawing Sheet

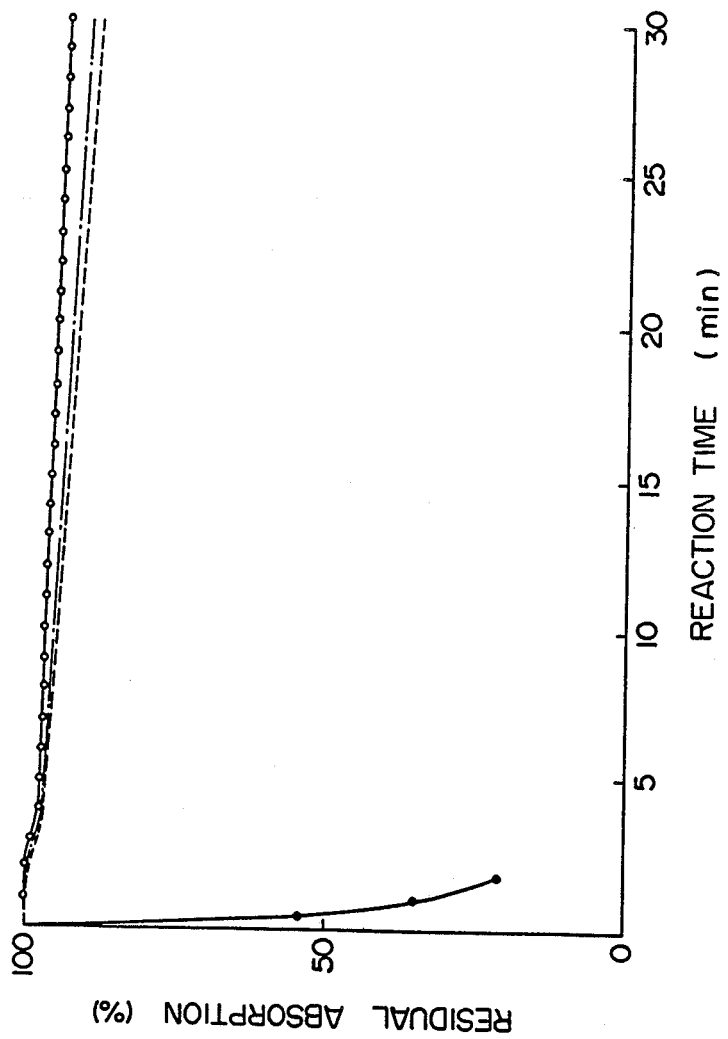

6-(DISUBSTITUTED AMINO)CARBAPENAM COMPOUNDS

This invention relates to 6-(disubstituted amino)carbapenam compounds, and more specifically, to compounds represented by the following formula

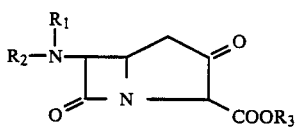

wherein $R_1$ represents a lower alkyl group or a lower haloalkyl group; $R_2$ represents a lower alkyl group, a lower haloalkyl group, an aralkyl group, or a group of the formula —COOR or —SO$_2$R$_5$ in which $R_4$ represents an alkyl group or a substituted or unsubstituted aralkyl group and $R_5$ represents an alkyl group or a substituted or unsubstituted aryl group; and $R_3$ represents a hydrogen atom or a carboxyl protecting group which can be easily split off,
and novel intermediates useful for the production of the above compounds.

Conventional carbapenem-series antibiotics commonly have the defect of being decomposed by dehydropeptidase. Compounds of formula (I) provided by this invention are useful as intermediates for the production of novel 6-(disubstituted amino)carbapenem-series antibiotics which are free from this common defect.

6-(Unsubstituted or monosubstituted amino)carbapenem compounds represented by the following general formula

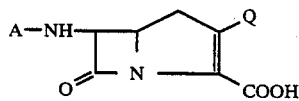

wherein A represents a hydrogen atom or an acyl group, and Q represents a hydrogen or halogen atom, or a substituent such as an alkyl, aryl, aralkyl, alkoxy or alkylthio group,
have previously been known as 6-aminocarbapenem-series antibiotics (see U.S. Pat. Nos. 4,218,459, 4,218,463, and 4,298,741).

The known 6-(monosubstituted amino)carbapenem compounds, however, are very unstable, and difficult to synthesize in practice.

The present inventors made extensive investigations in search of carbapenem-series antibiotics which are stable chemically and to dehydropeptidase. These investigations have led to the discovery that a certain class of 6-(disubstituted amino)carbapenem compounds are very stable chemically and to dehydropeptidase, and that the compounds of formula (I) above are important as intermediates for their synthesis.

The term "lower", used herein to qualify a compound or an atomic grouping, means that the compound or atomic grouping so qualified have not more than 6 carbon atoms, preferably not more than 4 carbon atoms.

The "alkyl group" or the alkyl moiety of the "haloalkyl group" may be linear or branched, and includes, for example, methyl, ethyl, n-propyl, isopropyl, n-butyl, isobutyl, sec-butyl, tert-butyl, n-pentyl, isoamyl, n-hexyl, n-octyl and 2-ethylhexyl groups. The halogen moiety in the "haloalkyl group" is, for example, a fluorine or chlorine atom. Examples of the "haloalkyl group" therefore include trifluoromethyl, trichloromethyl, trifluoroethyl, difluoroethyl, fluoroethyl and heptafluoropropyl groups.

Examples of the "aralkyl group" include benzyl, phenethyl and dibenzyl groups, and examples of the "aryl group" include phenyl and naphthyl groups. Examples of a substituent which may exist on the aromatic ring in the aralkyl and aryl group are halogen atoms such as a fluorine atom, lower alkyl groups such as methyl and ethyl groups, lower haloalkyl groups such as a trifluoromethyl group, lower alkoxy groups such as a methoxy group, a nitro group and an amino group.

Preferred groups $R_1$ in formula (I) include lower alkyl groups, and preferred $R_2$ groups include —COOR$_4$ in which $R_4$ represents a lower alkyl group or a benzyl group, and —SO$_2$R$_5$ in which $R_5$ represents a lower alkyl group.

The "carboxyl protecting group which can be easily split off" represented by $R_3$ in formula (I) is preferably a protective group for the carboxyl group which can be easily split off by, for example, hydrolysis or hydrogenolysis. Specific examples are (1) substituted or unsubstituted alkyl, alkenyl or alkynyl groups,
(2) cycloalkyl groups,
(3) cycloalkyl-alkyl groups,
(4) substituted or unsubstituted aryl groups, and
(5) substituted or unsubstituted aralkyl groups. These groups will be described below in detail.

(1) Substituted or unsubstituted alkyl, alkenyl or alkynyl groups (1-1) Desirably, the alkyl groups have 1 to 14 carbon atoms, preferably 1 to 12 carbon atoms, more preferably 1 to 10 carbon atoms, and may be linear or branched. Typical examples of the alkyl groups include methyl, ethyl, n-butyl, tert-butyl, n-pentyl, iso-amyl, n-hexyl, n-heptyl, n-octyl, 2-ethylhexyl, n-nonyl, n-decyl, n-undecyl and n-dodecyl.

(1-2) The alkenyl groups may be linear or branched, and contain 2 to 10 carbon atoms, preferably 2 to 6 carbon atoms. Lower alkenyl groups are suitable. Examples of such alkenyl groups are vinyl, allyl, 2-butenyl and 3-methyl-2-butenyl groups.

(1-3) The alkynyl groups are unsaturated aliphatic hydrocarbon groups having a triple bond in the carbon chain. Lower alkynyl groups are especially preferred in this invention. Examples include propargyl and ethynyl groups.

(1-4) The alkyl, alkenyl and alkynyl groups, particularly the alkyl groups, may be substituted by a group selected from the class consisting of halogen atoms, a hydroxyl group, lower alkoxy groups, lower alkylthio groups, cycloalkyloxy groups having 3 to 12 carbon atoms, cycloalkylthio groups having 3 to 12 carbon atoms, aryloxy groups (the aryl moiety is preferably a phenyl group and may be substituted by a halogen atom, a lower alkoxy group, a lower haloalkyl group or a nitro group), arylthio groups (the aryl moiety is preferably a phenyl group and may be substituted by a halogen atom, a lower alkoxy group, a lower haloalkyl group or a nitro group), di(C$_{1-10}$ alkyl)amino groups, acylamino groups having 2 to 16 carbon atoms, aroylimino groups, acyloxy groups having 2 to 16 carbon atoms, acylthio groups having 2 to 16 carbon atoms, acyl groups having 2 to 16 carbon atoms, alkoxycarbonyl groups having 2 to 14 carbon atoms (the alkoxy group may be substituted by a halogen atom) and aralkyloxycarbonyl groups having 8 to 24 carbon atoms (the aralkyl group may be substituted by a halogen atom, a lower alkoxy group, a lower haloalkyl group or a nitro group).

The acyl moiety in the "acylamino groups", "aroyl", "acyloxy groups", "acylthio groups" and "acyl groups" means the group $R_8CO-$ resulting from removal of OH from an organic carboxylic acid. Examples of the group $R_8$ are alkyl, cycloalkyl, aryl and aralkyl groups which may be substituted by substituents such as halogen atoms, lower alkoxy groups, lower haloalkyl groups, a nitro group, and di(lower alkyl)amino groups.

Typical examples of alkyl groups having such substituents include 2,2,2-trichloroethyl, 2,2,2-trifluoroethyl, hydroxyethyl, 2-hydroxypropyl, methoxymethyl, ethoxymethyl, isopropoxymethyl, ethoxyethyl, ethoxypropyl, methylthiomethyl, ethylthiomethyl, ethylthioethyl, methylthiopropyl, isopropylthioethyl, cyclohexyloxymethyl, cyclohexylthiomethyl, phenoxymethyl, phenoxyethyl, p-chlorophenoxymethyl, p-methoxyphenoxymethyl, p-trifluoromethylphenoxymethyl, p-nitrophenoxymethyl, phenylthiomethyl, p-methoxyphenylthiomethyl, p-trifluoromethylphenylthiomethyl, p-nitrophenylthiomethyl, 2-dimethylaminoethyl, 3-diethylaminopropyl, acetylaminomethyl, propionylaminomethyl, phthaloyliminomethyl, acetoxymethyl, acetoxyethyl, propionyloxymethyl, acetoxypropyl, pivaloyloxymethyl, benzoyloxymethyl, trichloroacetoxymethyl, dimethylaminoacetoxymethyl, p-methoxybenzoyloxymethyl, p-nitrobenzoyloxymethyl, phenylacetoxymethyl, acetylthiomethyl, acetylthioethyl, acetonyl, propionylmethyl, phenacyl, p-chlorophenacyl, p-bromophenacyl, p-methylphenacyl, p-tert-butylphenacyl, p-ethylphenacyl, p-nitrophenacyl, o-nitrphenacyl, p-trifluoromethylphenacyl, p-methoxyphenacyl, benzoylethyl, phenylacetonyl, methoxycarbonylmethyl, ethoxycarbonylmethyl, carbamoylmethyl, carbamoylethyl, tert-butoxycarbonylmethyl, tert-amyloxycarbonylmethyl, 2,2,2-trichloroethoxycarbonylmethyl, 2,2,2-tribromoethoxycarbonylmethyl, benzyloxycarbonylmethyl, diphenylmethoxycarbonylmethyl, triphenylmethoxycarbonylmethyl, p-nitrobenzyloxycarbonylmethyl, p-nitrobenzyloxycarbonylethyl, p-methoxybenzyloxycarbonylmethyl, phenethyloxycarbonylmethyl, and 2-amino-2-p-nitrobenzyloxycarbonylethyl groups.

(2) Cycloalkyl groups

Suitable cycloalkyl groups contain 3 to 15 carbon atoms, preferably 3 to 10 carbon atoms, more preferably 3 to 6 carbon atoms. They may include cycloalkyl groups having a lower alkyl group on the ring. Typical examples of the cycloalkyl groups are cyclopropyl, cyclobutyl, cyclopentyl, cyclohexyl, cycloheptyl, cyclooctyl, 4-methylcyclohexyl and 4-ethylcyclohexyl groups.

(3) Cycloalkyl-alkyl groups

The cycloalkyl-alkyl groups are preferably those in which the cycloalkyl moiety has the meaning described in (2) above, and the alkyl moiety is a lower alkyl group. Specifically, cycloalkyl-alkyl groups having 4 to 19 carbon atoms, preferably 4 to 14 carbon atoms, particularly 4 to 10 carbon atoms, are suitable. Examples of such cycloalkyl-alkyl groups are cyclopentylmethyl, cyclohexylmethyl, cyclohexylethyl and cycloheptylmethyl groups.

(4) Substituted or unsubstituted aryl groups (4-1) The aryl groups may be monocyclic or polycyclic and usually contain 6 to 18 carbon atoms, preferably 6 to 14 carbon atoms, more preferably 6 to 10 carbon atoms. Typical examples of the aryl groups are phenyl, tolyl, xylyl and naphthyl.

(4-2) The aryl groups may have a substituent on the aromatic ring. Examples of the substituent are halogen atoms, lower alkoxy groups, aryloxy groups, lower haloalkyl groups, acyloxy groups, acylamino groups, a carboxyl group, lower alkoxycarbonyl groups, a hydroxyl group and a nitro group.

Examples of aryl groups substituted by these substituents include p-chlorophenyl, p-methoxyphenyl, p-trifluoromethylphenyl, p-acetyloxyphenyl, p-acetylaminophenyl, p-methoxycarbonylphenyl, p-nitrophenyl, and 2,4-dinitrophenyl groups.

(5) Substituted or unsubstituted aralkyl groups (5-1) The aralkyl groups may be monocyclic or polycyclic, and the alkyl moiety is preferably a lower alkyl group. The aralkyl groups may usually contain 7 to 25 carbon atoms, preferably 7 to 22 carbon atoms, more preferably 7 to 19 carbon atoms. Examples of such aralkyl groups include benzyl, p-tert-butylbenzyl, p-methylbenzyl, 2,4-dimethylbenzyl, 2,4,6-trimethylbenzyl, benzhydryl, 1,1-diphenylethyl, 1,1-diphenylpropyl, 1,1-diphenylbutyl, trityl and p-methyltrityl groups.

(5-2) A substituent may be present on the aromatic ring of the aralkyl group. Suitable examples of the substituent are halogen atoms, lower alkoxy groups, aryloxy groups, lower haloalkyl groups, acyloxy groups, acylamino groups, a carboxyl group, carboxylate salt groups, lower alkoxycarbonyl groups, a hydroxyl group and a nitro group. Typical examples of the aralkyl groups substituted by these substituents include p-chlorobenzyl, p-bromobenzyl, p-methoxybenzyl, p-tert-butoxybenzyl, 3,5-bis-tert-butoxy-4-hydroxybenzyl, m-phenoxybenzyl, p-trifluoromethylbenzyl, o- or p-pivaloyloxybenzyl, p-acetoxybenzyl, p-benzoyloxybenzyl, p-2-ethylhexanoylbenzyl, p-benzamidobenzyl, p-methoxycarbonylbenzyl, p-ethoxycarbonylbenzyl, p-butoxycarbonylbenzyl, p-hydroxybenzyl, o- or p-nitrobenzyl, p-chlorobenzhydryl, p-methoxybenzhydryl, p-acetoxybenzhydryl, p-nitrobenzhydryl, m- or p-chlorotrityl, p-bromotrityl, p-methoxytrityl, p-ethoxytrityl and p-nitrotrityl.

Typical examples of the compounds of formula (I) provided by this invention are given below.

p-Nitrobenzyl 3,7-dioxo-6-[N-methyl-N-methoxycarbonyl]amino-1-azabicyclo[3.2.0]heptane-2-carboxylate, p-nitrobenzyl 3,7-dioxo-6-[N-benzyloxycarbonyl-N-methyl]amino-1-azabicyclo[3.2.0]heptane-2-carboxylate, p-nitrobenzyl 3,7-dioxo-6-[N-ethoxycarbonyl-N-methyl]amino-1-azabicyclo[3.2.0]heptane-2-carboxylate, p-nitrobenzyl 3,7-dioxo-6-[N-tert-butoxycarbonyl-N-methyl]amino-1-azabicyclo[3.2.0]heptane-2-carboxylate, p-nitrobenzyl 3,7-dioxo-6-[N-methyl-N-p-nitrobenzyloxycarbonyl]amino-1-azabicyclo]3.2.0]heptane-2-carboxylate, p-nitrobenzyl 3,7-dioxo-6-[N-ethyl-N-methoxycarbonyl]amino-1-azabicyclo[3.2.0]heptane-2-carboxylate, p-nitrobenzyl 3,7-dioxo-6-[N-trifluoromethyl-N-methoxycarbonyl]amino-1-azabicyclo[3.2.0]heptane-2]-carboxylate, p-nitrobenzyl 3,7-dioxo-6-[N-trifluoroethyl-N-methoxycarbonyl]amino-1-azabicyclo[3.2.0]heptane-2-carboxylate,
p-nitrobenzyl 3,7-dioxo-6-[N-fluoroethyl-N-methoxycarbonylamino-1-azabicyclo[3.2.0]heptane-2-carboxylate,
p-nitrobenzyl 3,7-dioxo-6-[N-propyl-N-methoxycabonyl]amino-1-azabicyclo[3.2.0]heptane-2-carboxylate,
p-nitrobenzyl 3,7-dioxo-6-[N-trifluoromethyl-N-ethoxycarbonyl]amino-1-azabicyclo[3.2.0]heptane-2-carboxylate,
p-nitrobenzyl 3,7-dioxo-6-[N-methyl-N-methanesulfonyl]amino-1-azabicyclo[3.2.0]heptane-2-carboxylate,
p-nitrobenzyl 3,7-dioxo-6-[N-methyl-N-ethanesulfonyl]amino-1-azabicyclo[3.2.0]heptane-2-carboxylate,
p-nitrobenzyl 3,7-dioxo-6-[N-methyl-N-benzenesulfonyl]amino-1-azabicyclo[3.2.0]heptane-2-carboxylate,
p-nitrobenzyl 3,7-dioxo-6-[N-methyl-N-toluenesulfonyl]amino-1-azabicyclo[3.2.0]heptane-2-carboxylate,
p-nitrobenzyl 3,7-dioxo-6-[N-methyl-N-p-fluorobenzenesulfonyl]amino-1-azabicyclo[3.2.0]heptane-2-carboxylate,
p-nitrobenzyl 3,7-dioxo-6-[N-trifluoromethyl-N-methanesulfonyl]amino-1-azabicyclo[3.2.0]heptane-2-carboxylate,
p-nitrobenzyl 3,7-dioxo-6-[N-ethyl-N-methanesulfonyl]amino-1-azabicyclo[3.2.0]heptane-2-carboxylate,
p-nitrobenzyl 3,7-dioxo-6-[N-fluoroethyl-N-methanesulfonyl]amino-1-azabicyclo[3.2.0]heptane-2-carboxylate,
p-nitrobenzyl 3,7-dioxo-6-[N,N-dimethyl]amino-1-azabicyclo[3.2.0]heptane-2-carboxylate,
p-nitrobenzyl 3,7-dioxo-6-[N-methyl-N-ethyl]amino-1-azabicyclo[3.2.0]heptane-2-carboxylate,
p-nitrobenzyl 3,7-dioxo-6-[N-methyl-N-propyl]amino-1-azabicyclo[3.2.0]heptane-2-carboxylate,
p-nitrobenzyl 3,7-dioxo-6-[N-methyl-N-trifluoromethyl]amino-1-azabicyclo[3.2.0]heptane-2-carboxylate,
p-nitrobenzyl 3,7-dioxo-6-N-methyl-N-fuoroethyl]amino-1-azabicyclo[3.2.0]heptane-2-carboxylate,
p-nitrobenzyl 3,7-dioxo-6-[N,N-diethyl]amino-1-azabicyclo[3.2.0]heptane-2-carboxylate,
p-nitrobenzyl 3,7-dioxo-6-[N-ethyl-N-trifluoroethyl]amino-1-azabicyclo[3.2.0]heptane-2-carboxylate,
p-nitrobenzyl 3,7-dioxo-6-[N-ethyl-N-fluoroethyl]amino-1-azabicyclo[3.2.0]heptane-2-carboxylate,
p-nitrobenzyl 3,7-dioxo-6-[N-methyl-N-benzyl]amino-1-azabicyclo[3.2.0]heptane-2-carboxylate, and
p-nitrobenzyl 3,7-dioxo-6-[N-ethyl-N-benzyl]amino-1-azabicyclo[3.2.0]heptane-2-carboxylate.

The compound of formula (I) has three asymmetric carbon atoms at the 2-, 5- and 6-positions, and stereoisomers shown below exist.

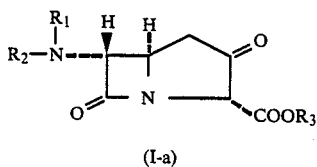

(I-a)

-continued

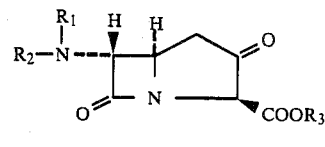

(I-b)

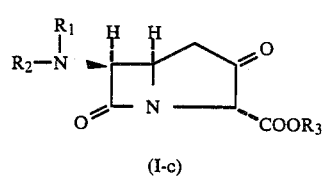

(I-c)

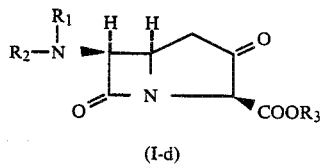

(I-d)

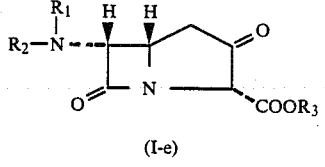

(I-e)

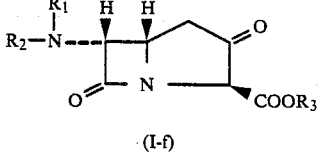

(I-f)

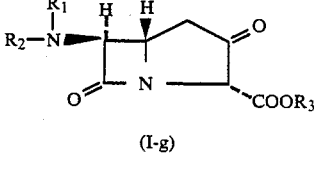

(I-g)

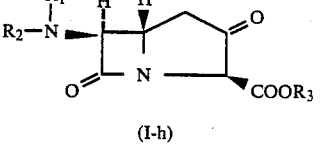

(I-h)

The compounds of formula (I) provided by this invention include all of these isomers. Among them, the isomers of formula (I-a) and (I-b) are especially preferred.

The compounds provided by this invention are novel compounds not described in the prior literature. They can be synthesized by the route shown by Reaction Scheme A given below starting from compounds of formula (II) which are known per se or can be produced as in the production of known compounds of formula (II).

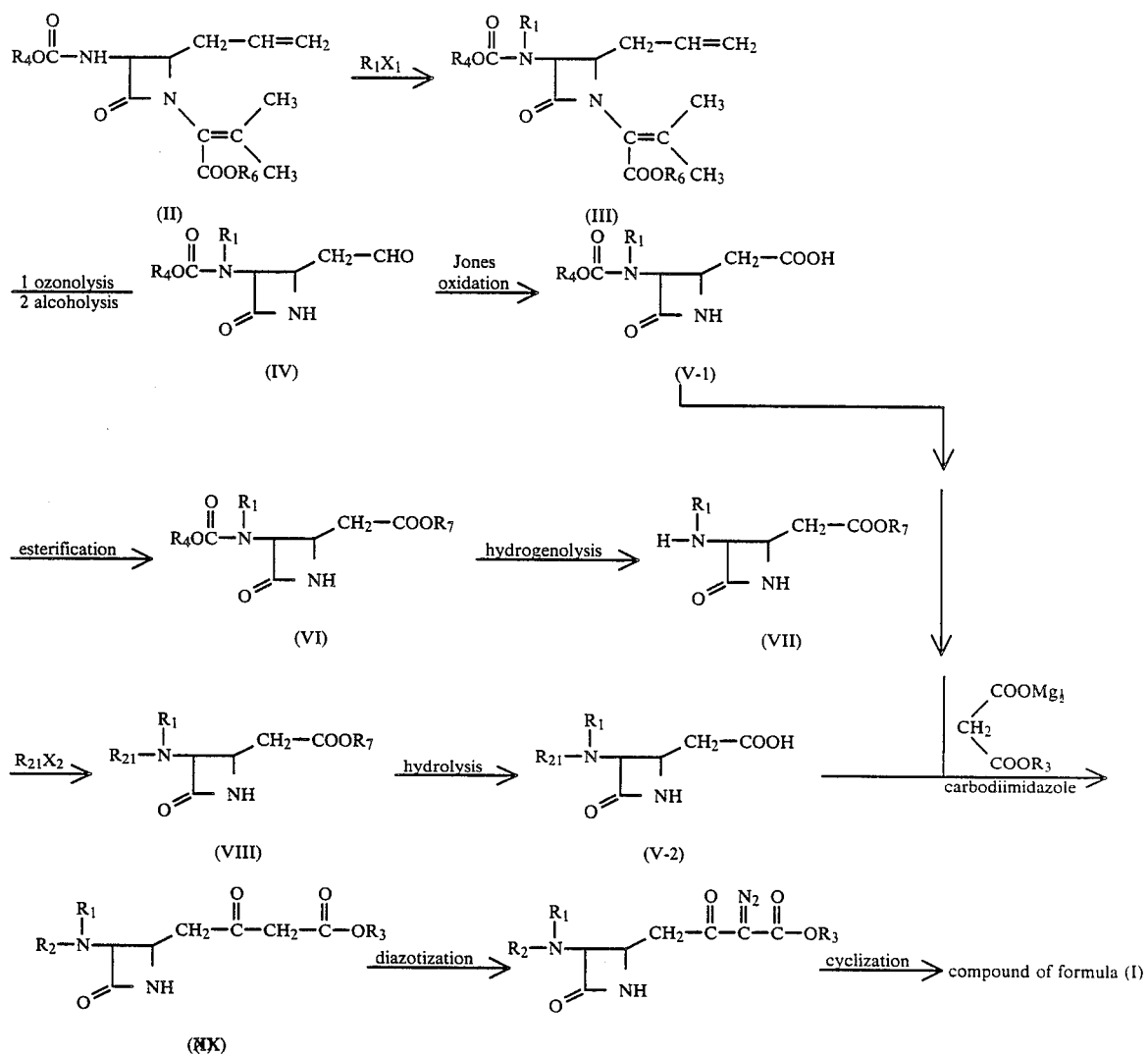

Reaction Scheme A

In the above scheme, $X_1$ and $X_2$ each represent a halogen atom, $R_6$ and $R_7$ represent a carboxyl protecting group such as an alkyl group, $R_{21}$ represents groups defined for $R_2$ hereinabove other than $-COOR_4$ in formula (V-1), and $R_1$, $R_2$ and $R_3$ are as defined hereinabove.

The compound of formula (II) see, for example, M. Aratani et al., Tetrahedron Letters, Vol. 26, No. 2, pp. 223–226 (1985)] is N-alkylated with $R_1X_1$. The N-alkylation can be carried out by a method known per se, for example the method described in M. E. Kuehne et al., J. Am. Chem. Soc., 83, 1492 (1961), by reacting the compound of formula (I) with a lower alkyl halide ($R_1X_1$) such as methyl iodide at a temperature of 25° to 40° C. in a suitable inert solvent.

The resulting compound can be converted to the compound of formula (IV) by ozonolysis and subsequent alcoholysis. The ozonolysis gives a compound of the following formula Alcoholysis of this compound with, for example, methanol gives the compound of formula (IV). The ozonolysis and alcoholysis can be carried out by methods known per se, for example the method described in Aratani et al., Tetrahedron Letters, 26, 223 (1985). The ozonolysis can be carried out, for example, by contacting the compound of formula (III) with an ozone gas at about −70° to −60° C. in a suitable inert solvent. The product can be heated under reflux with an alcohol such as methanol without isolation to form the compound of formula (IV).

The resulting compound of formula (IV) is subjected to Jones oxidation to form the compound of formula (V-1). The Jones oxidation may also be carried out by a method known per se [see, for example, D. J. Hart et al., Tetrahedron Letters, 26, 5493 (1985)] by treating the compound of formula (IV) with a sulfuric acid solution of chromium trioxide.

The substituent —COOR$_4$ at the amino group at the 3-position of the compound of formula (V-1) so obtained can be replaced by the other substituents defined for R$_2$ hereinabove. Specifically, the compound of formula (V-1) is esterified to protect the carboxyl group in the 4-position side chain [the compound of formula (VI)]. It is then hydrogenolyzed in accordance with a method known per se, for example by contacting it with hydrogen in the presence of a 10% Pd-C catalyst at room temperature under atmospheric or elevated pressure to split off the group —COOR$_4$ [the compound of formula (VII)]. It is then reacted with a compound of the formula R$_{21}$X$_2$ such as an alkyl chloroformate, mesyl chloride, tosyl bromide and methyl iodide. Finally, the carboxyl protecting group is split off by hydrolysis, etc. to give the compound of formula (V-2).

The compounds of formulae (V-1) and (V-2), i.e. compounds of the following formula

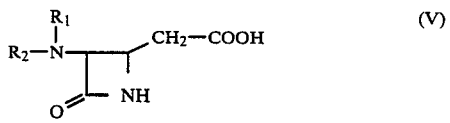
(V)

where R$_1$ and R$_2$ are as defined above, are important intermediates for synthesis of the compounds of formula (I) and/or the aforesaid di-(substituted amino)carbapenem-series antibiotics.

The compound of formula (V) is then reacted with carbodiimidazole to activate the carboxyl group in the 4-position side chain, and then reacted with monomagnesium malonate of the following formula

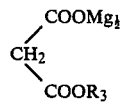

by a method known per se [see, for example, D. G. Melillo et al., Tetrahedron Letters, 21, 2783 (1980)] to convert it into the compound of formula (IX).

The compound of formula (IX) can be converted into the compound of formula (X) in accordance with the method described in the above-cited literature reference, for example by treating it with tosyl azide in the presence of an organic base.

Cyclization of the compound of formula (X) can be carried out by heating it at the refluxing temperature in the presence of rhodium acetate dimer in the presence of a suitable inert solvent. As a result, the compound of formula (I) can be obtained.

The compound of formula (I) so formed can be separated and purified by means known per se, for example by chromatography, solvent extraction or recrystallization.

The compounds of formula (I) provided by this invention are useful as intermediates for production of 6-(disubstituted amino)carbapenem-series antibiotics which are stable chemically and to dehydropeptidase, for example compounds of the following formula

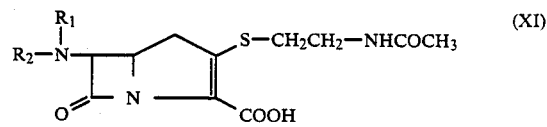
(XI)

and their salts. Conversion of the compounds of formula (I) into the compounds of formula (XI) can be carried out by the route shown by Reaction Scheme B below. In performing this reaction, the compound of formula (I) may be directly subjected to the next reaction without isolation and purification. Details of this reaction are described in Examples 11 to 13, 19 to 21, 26 to 28, and 33 to 35.

Reaction Scheme B

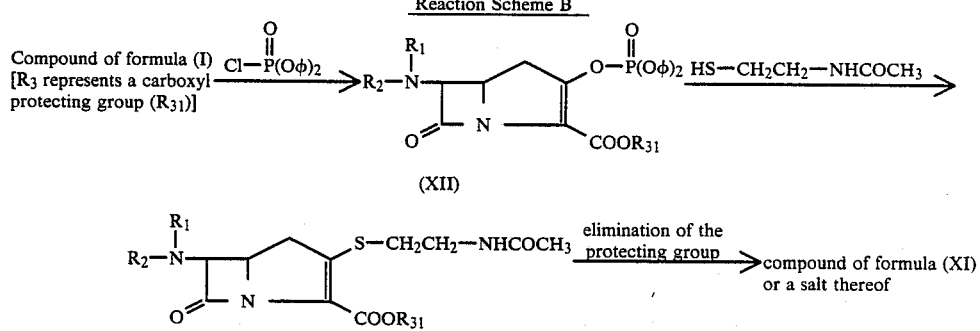

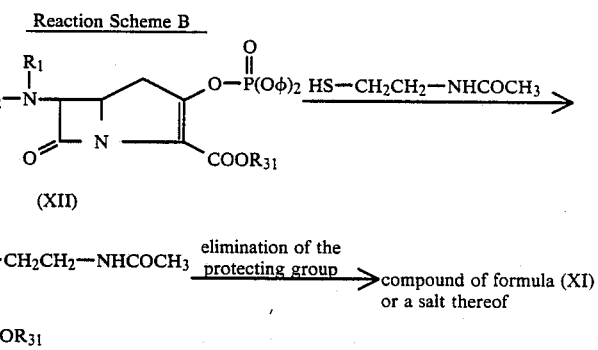

In the above scheme, $\phi$ represents a phenyl group, and R$_1$ and R$_2$ are as defined hereinabove.

The compound of formula (XI) obtained by the above reaction has good antimicrobial activity shown by test results given below and is very stable without the defect of being decomposed with dehydropeptidase which is commonly seen in conventional carbapenem-series antibiotics. Hence, it is useful as an antimicrobial agent.

(1) Antimicrobial activity test

The antimicrobial activity was measured by the agar diluting method in accordance with the Standardised Method of the Japanese Society of Chemotherapy. A twofold dilution of a test compound was prepared by using M/50 phosphate buffer (pH 7.0). One milliliter of this solution and 9 ml of a Mueller Hinton agar medium (made by Difco Laboratories) were mixed in a Petri dish having a diameter of 9 cm to prepare plates. A test microorganism was cultured overnight in a stationary condition at 35° C. in a Mueller-Hinton broth (made by Difco) and diluted with physiological saline to provide a cell density of about 10$^6$ cells/ml. Five microliter of the microorganism suspension was inoculated on the agar plates using a microplanter (made by Sakuma Seisakusho). The plates were incubated at 35° C. for 18 hours. The lowest concentration of the test compound at which the growth of the microorganism was completely inhibited is defined as the minimum inhibitory concentration (MIC) of the test compound against the test organism.

The results are shown in Table 1.

TABLE 1

| | MIC (μg/ml) | | |
| --- | --- | --- | --- |
| | Test compound | | |
| Test organism | Compound [14] of Example 13 | Compound [22] of Example 21 | Compound [29] of Example 28 |
| Bacillus subtilis (ATCC 6633) | 1.56 | 6.25 | 1.56 |
| Micrococcus luteus (ATCC 9341) | 1.56 | 3.13 | 0.78 |
| Staphylococcus aureus (FDA 209p) | 0.20 | 0.39 | 0.20 |
| Comamonas terrigena (B 996) | 1.56 | 0.39 | 3.13 |

(2) Test for stability to kidney dehydropeptidase-I (cuvette asay)

An acetone powder was prepared from a microsome fraction of dog kidneys. To 250 mg of the acetone powder was added 25 ml of 20% butanol-M/20 Tris-HCl buffer (pH 7.0), and the mixture was stirred vigorously at 5° C. for 2 hours. The mixture was dialyzed against 5 liters of water three times.

The above enzyme solution (0.2 ml) was mixed with 0.2 ml of a test compound solution prepared in a concentration of 1 mg/ml by using M/10 Tris-hydrochloric acid buffer (pH 7.0). In a quartz cuvette having a light path length of 1.0 mm and kept at 37° C., the decrease in absorption at 300 and 340 nm was monitored by a Hitachi double beam spectrophotometer (model 200-100). The O.D. at the start of the reaction was taken as 100%, and the stability of the test compound was examined by the percent O. D. at each reaction time.

The results are shown in FIG. 1. In the figure, —■——■— shows the results obtained on an antibiotic PS-5; —○——○—, the results obtained on compound [22]; —•——•—, the results obtained on [14]; and ————————, the results obtained on compound [29].

It is seen from FIG. 1 that the compound of this invention is useful as an intermediate for synthesis of a compound which has such a stability to kidney dehydropeptidase as to be unable to be anticipated from a conventional carbapenem-series antibiotic.

The following Examples illustrate the present invention more specifically.

EXAMPLE 1

Production of (2S, 5R, 6R)-3,3-dimethyl-2-methoxycarbonyl-7-oxo-6-phthalimide-4-thia-1-azabicyclo[3.2.0]heptane [2]

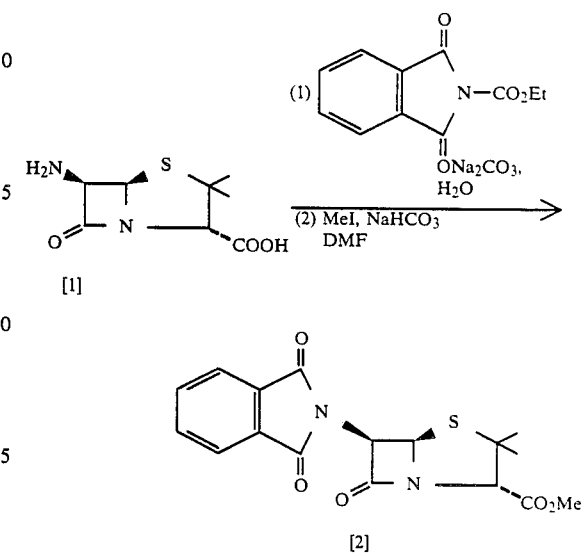

50.6 g (234 mmol) of 6-aminopenicillanic acid [1] was dissolved in 400 ml of water containing 24.8 g (234 mmol) of sodium carbonate, and 61.6 g (280 mmol) of N-carboethoxyphthalimide was added, and the mixture was vigorously stirred at room temperature for 16 hours.

The reaction mixture was washed once with methylene chloride, and 4N hydrochloric acid was added to adjust the pH of the solution to about 2. It was extracted with methylene chloride three times. The organic layers were combined, washed twice with water, and dried over sodium sulfate.

The solvent was evaporated to give 76.4 g of a crude carboxylic acid. It was dissolved in 500 ml of N,N-dimethylformamide, and 37.1 g (441 mmol) of sodium hydrogen carbonate and 27.5 ml (441 mmol) of methyl iodide were added, and the mixture was stirred at room temperature for 16 hours.

The reaction mixture was concentrated under reduced pressure, and the residue as separated with methylene chloride-water. The aqueous layer was again extracted with methylene chloride. The organic layers were combined, and washed successively with water and a saturated aqueous solution of sodium chloride, and dried over sodium sulfate. The solvent was evaporated to form 80 g of a crystalline residue. It was recrystallized from boiling acetone to give 48.2 g (57%) of the captioned compound as white crystals.

Melting point: 174°-177.5° C.

$^1$H NMR (CDCl$_3$) δ1.51 (3H, s, C$_2$-methyl), 1.81 (3H, s, C$_2$-methyl), 3.79 (3H, s, CO$_2$CH$_3$), 4.63 (1H, s, H-2), 5.52 (1H, d, J=4 Hz, H-5), 5.61 (1H, d, J=4 Hz, H-6), 7.6–7.9 (4H, m, phenyl).

EXAMPLE 2

Production of (2S, 5R, 6S)-3,3-dimethyl-2-methoxycarbonyl-7-oxo-6-phthalimide-4-thia-1-azabicyclo[3.2.0]heptane [3]

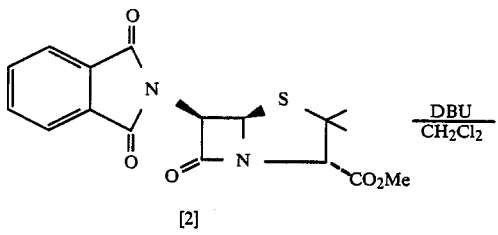

130 g (0.361 mol) of (2S, 5R, 6R)-3,3-dimethyl-2-methoxycarbonyl-7-oxo-6-phthalimide-4-thia-1-azabicyclo[3.2.0]heptane [2] was dissolved in 1 liter of methylene chloride, and 5 ml (33.4 mmol) of 1,8-diazabicyclo[5.4.0]undec-7-ene was added, and the mixture was stirred at room temperature for 16 hours.

The reaction mixture was washed with 500 ml of a cold 0.1N aqueous solution of hydrochloric acid, washed with 500 ml of water, and dried over sodium sulfate. The solvent was evaporated, and the resulting crystalline residue was recrystallized from benzene to give 90 g of the captioned compound as white crystals.

The crystallization mother liquor was concentrated, and the resulting residue was adsorbed on a column of silica gel (400 g). The column was eluted with benzene/ethyl acetate (10/1). Those fractions in the eluates which showed a UV absorption in silica gel TLC developed with benzene/ethyl acetate (5/1) were collected and concentrated under reduced pressure to give 38 g (total 128 g; 98.5%) of the captioned compound as a crystalline residue.

Melting point: 184°-185° C.

IR $\nu_{max}^{CHCl_3}$ 1785 (shoulder), 1775, 1725cm$^{-1}$ $^1$H NMR (CDCl$_3$) δ1.47 (3H, s, C$_2$ methyl), 1.64 (3H, s, C$_2$ methyl), 3.76 (3H, s, CO$_2$CH$_3$), 4.58 (1H, s, H-2), 5.34 (1H, d, J=2 Hz, H-5), 5.52 (1H, d, J=2 Hz, H-6), 7.6–7.9 (4H, m, phenyl).

EXAMPLE 3

Production of (2S,4R)- and (3S, 4S)-4-chloro-1-(1-methoxycarbonyl-3-methyl-1-propenyl)-3-phthalimide-2-azetidinone [4]

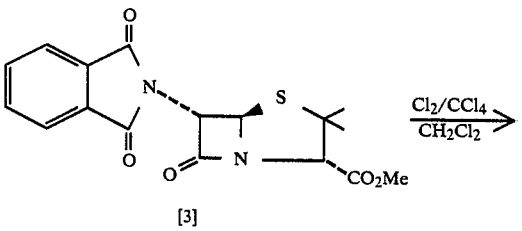

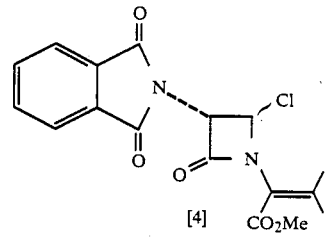

Seventy grams (194 mmol) of (2R, 5R, 6S)-3,3-dimethyl-2-methoxycarbonyl-7-oxo-6-phthalimide-4-thia-1-azabicyclo[3.2.0]heptane [3] was dissolved in 700 ml of methylene chloride. The solution was coled to −60° C., and a solution (150 ml) of carbon tetrachloride containing 25 ml of chlorine was added dropwise to the cooled solution. The reaction solution was stirred at −60° C. for 1 hour and then at room temperature for 1 hour. The reaction mixture was diluted with methylene chloride, and washed with a cold saturated aqueous solution of sodium hydrogen carbonate three times and thereafter with water two times. The washed product was dried over sodium sulfate. The solvent was evaporated, and the resulting syrup was adsorbed on a column of silica gel (750 g) using a small amount of methylene chloride. The column was eluted stepwise with benzene/ethyl acetate (30/1, 20/1). Those fractions in the eluates which showed a UV absorption at an Rf of 0.54 in silica gel TLC developed with benzene/ethyl acetate (4/1) were collected and concentrated under reduced pressure to give 42.3 g (60%) of the captioned compound as a colorless syrup.

The ratio of the (3S, 4R) isomer (trans) to the (3S,4S) isomer (cis) was found to be about 2:1 by $^1$H NMR.

IR δ$_{max}^{CHCl_3}$ 1790, 1770, 1720cm$^{-1}$.

$^1$H NMR (CDCl$_3$) δ2.07 (3H, s,

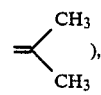), 2.30 (3H, s,

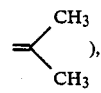), 3.74 (3×⅓H, s, cis-isomer Co$_2$Me), 3.81 (3×⅔H, s, trans-isomer Co$_2$Me), 5.53 (⅔H, d, J=1.5 Hz, trans-isomer H-3), 5.62 (⅓H, d, J=4.3 Hz, cis-isomer H-3), 6.15 (⅓H, d, J=4.3 Hz, cis-isomer H-4), 6.18 (⅔H, d, J=1.5 Hz, trans-isomer H-4), 7.55–7.85 (4H, m, phenyl).

EXAMPLE 4

Production of (3R, 4R)-1-(1-methoxycarbonyl-3-methyl-1-propenyl)-3-phthalimide-4-(2-propenyl)-2-azetidinone 5]

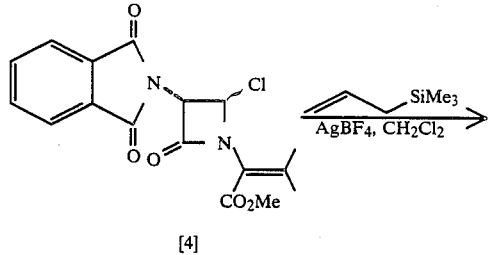

[4]

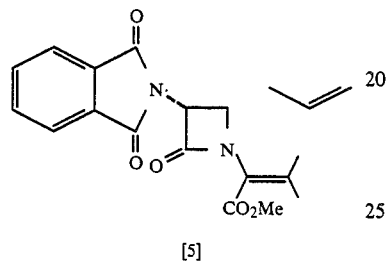

[5]

4.58 g (12.6 mmol) of (3S,4R)- and (3S,4S)-4-chloro-1-(1-methoxycarbonyl-2-methyl-1-propenyl)-3-phthalimide-2-azetidinone was dissolved in 100 ml of methylene chloride, and 3.05 ml (19.2 mmol) of allylsilane was added. The reaction solution was cooled to −60° C., and 2.8 g (12.6 mmol assuming that the purity was 90%) of silver tetrafluoroborate was added. The reaction mixture was heated to 0° C. over the course of about 2 hours. Then, it was stirred at 0° C. for 2 hours.

The insoluble materials were separated by filtration. The filtrate was washed successively with a cold saturated aqueous solution of sodium hydrogen carbonate twice, water once and a saturated aqueous solution of sodium chloride once, and then dried over sodium sulfate.

The solvent was evaporated, and the resulting syrup was dissolved in a small amount of methylene chloride and adsorbed on a column of silica gel (120 g). The column was eluted stepwise with benzene/ethyl acetate (20/1, 10/1 and 6/1). Those fractions in the eluates which showed a UV absorption at an Rf of 0.30 in TLC developed with benzene/ethyl acetate (4:1) were collected and concentrated under reduced pressure to give 3.72 g (80%) of the captioned compound as a colorless amorphous solid.

IR $\nu_{max}^{CHCl_3}$ 1780 (shoulder), 1760, 1720 cm$^{-1}$.

$^1$H NMR (CDCl$_3$) δ2.12 (3H, s,

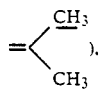

2.26 (3H, s,

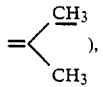

2.46 (2H, bt, J=7 Hz, methylene), 3.83 (3H, s, CO$_2$CH$_3$), 4.42 (1H, td, J=2.5 and 7.0 Hz, H-4), 4.9–5.2 (2H, m,=CH$_2$), 5.12 (1H, d, J=2.5 Hz, H-3), 5.43–5.90 (1H, m, $$\underset{\underline{H}}{\diagdown}=CH_2),$$

7.55–7.85 (4H, m, phenyl).

EXAMPLE 5

Production of (3R, 4R)-3-amino-1-(1-methoxycarbonyl-2-methyl-1-propenyl)-4-(2-propenyl)2-azetidinone[6]

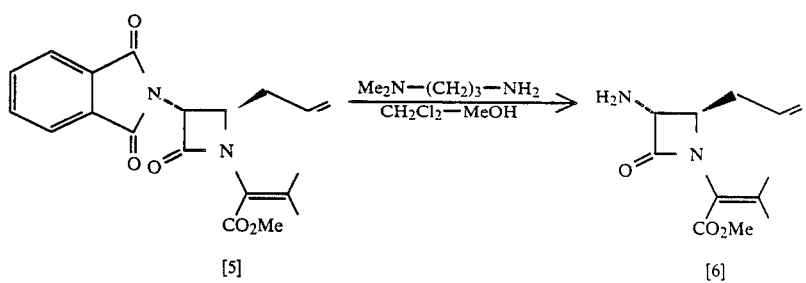

21.8 g (59.2 mmol) of (3R, 4R)-1-(1-methylxcarbonyl-2-methyl-1-propenyl)-3-phthalimide-4-(2-propenyl)-2-azetidinone [5] was dissolved in a mixed solvent composed of 140 ml of methanol and 140 ml of methylene chloride, and 16.4 ml (130 mmol) of dimethylaminopropylamine was added. The mixture was stirred at 40° to 45° C. for 17 hours.

The reaction mixture was concentrated under reduced pressure. The resulting syrup was dissolved in a small amount of methylene chloride, and adsorbed on a column of silica gel (600 g). The column was eluted stepwise with ethyl acetate/methanol (10/1, 8/1 and 6/1). Those fractions in the eluates which showed a UV absorption at an Rf of 0.52 in TLC developed with ethyl acetate/methanol (3/1) were collected, and concentrated under reduced pressure to give 10.9 g (77%) of the captioned compound as a colorless syrup.

IR $\nu_{max}^{CHCl_3}$ 3370, 1745, 1720 1640, 1630 cm$^{-1}$.

$^1$H NMR (CDCl$_3$) δ1.74 (2H, s, NH$_2$), 1.92 (3H, s,

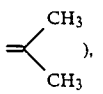

2.17 (3H, s,

2.37 (2H, bt, J~7 Hz, methylene), 3.6–3.8 (2H, m, H-3 and H-4), 3.73 (3H, s, CO$_2$Me), 4.9–5.2 (2H, m, vinyl), 5.4–6.0 (1H, m, vinyl)

EXAMPLE 6

Production of (3R, 4R)-3-benzyloxycarbonylamino-1-(1-methoxycarbonyl-2-methyl-1-propenyl)-4-(2-propenyl)-2-azetidinone [7]

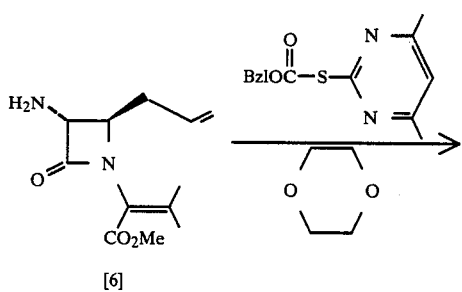

[6]

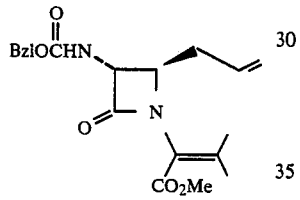

[7]

5.05 g (21.2 mmol) of (3R,4R)-3-amino-1-(1-methoxycarbonyl-2-methyl-1-propenyl)-4-(2-propenyl)-2-azetidinone [6] was dissolved in 30 ml of dioxane, and a dioxane solution (60 ml) of 6.4 g (23.3 mmol) of S-4,6-dimethylpyrimidin-2-ylthiocarbonate was added dropwise to the solution at room temperature. The mixture was stirred at room temperature for 16 hours. Benzene (100 ml) was added to the reaction solution, and the insoluble materials were separated by filtration. The filtrate was concentrated, and the resulting syrup was dissolved in a small amount of methylene chloride. The solution was adsorbed on a column of silicas gel (500 g), and the column was eluted stepwise with benzene and benzene/ethyl acetate (10/1, 5/1 and 3/1). Fractions in the eluates which showed a UV absorption at an Rf of 0.20 in TLC developed with benzene/ethyl acetate (4:1) were collected and concentrated under reduced pressure to give 7.66 g (97%) of the captioned compound as a colorless syrup.

IR $\nu_{max}^{CHHCl_3}$ 3410, 1755, 1715cm$^{-1}$ $^1$H NMR (CDCl$_3$) δ1.96 (3H, s,

2.22 (3H, s,

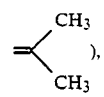

2.47 (2H, bt, J~6 Hz, methylene), 3.80 (3H, x, CO$_2$CH$_3$), 4.02 (1H, td, J=2.5 and 6 Hz, H-4), 4.62 (1H, m, H-3), 5.05 (1H, b, NH), 5.20 (2H, x, benzyl), 5.1–5.2 (1H, m, vinyl), 5.55–6.20 (2H, m, vinyl), 7.45 (5H, s, phenyl).

EXAMPLE 7

Production of (3R,4R)-3-(N-benzyloxycarbonyl)-methylamino-1-(1-methoxycarbonyl-2-methyl-1-propenyl)-4-(2-propenyl)-2-azetidinone [8]

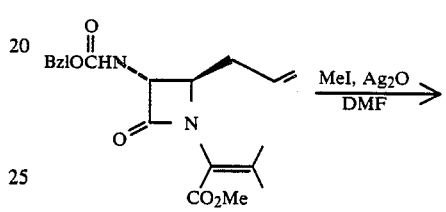

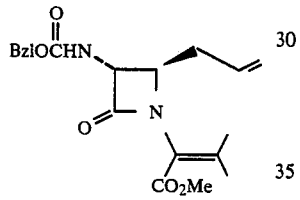

[7]

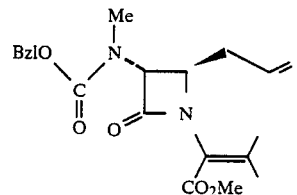

[8]

1.15 g (3.09 mmol) of (3R, 4R)-3-benzyloxycarbonylamino-1-(1-methoxycarbonyl-2-methyl-1-propenyl)-4-(2-propenyl)-2-azetidinone was dissolved in 20 ml of N,N-dimethylformamide. To the solution were added 3.58 g (15.5 mmol) of silver oxide and 3.85 ml (61.8 mmol) of methyl iodide. The reactor was sealed up and the reaction was carried out in the dark at 40° C. for 16 hours.

Ethyl acetate was added to the reaction solution, and the insoluble materials were separated by filtration, and washed with ethyl acetate. The filtrate and the washing were combined and concentrated under reduced pressure. The residue was dissolved in a small amount of methylene chloride and adsorbed on a column of silica gel (60 g). The column was eluted stepwise with benzene/ethyl cetate (10/1, 5/1 and 3/1). Those fractions in the eluate which showed a UV absorption at an Rf of 0.41 in TLC developed with benzene/ethyl acetate (3/1) were collected and concentrated under reduced pressure to obtain 1.00 g (92 %) of the captioned compound as a colorless syrup.

IR $\nu_{max}^{CHCl_3}$ 1755, 1730 (shoulder), 1700 cm$^{-1}$.

$^1$H NMR (CDCl$_3$) δ1.93 (3H, s,

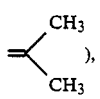

2.20 (3H, s,

2.37 (2H, m, methylene), 3.01 (3H, s, NMe), 3.74 (3H, s, CO$_2$CH$_3$), 3.98 (1H, td, J=2.5 and 6.0 Hz, H-4), 4.8–5.2 (3H, m, vinyl, H-3), 5.14 (2H, s, benzyl), 5.3–5.8 (1H, m, vinyl), 7.34 (5H, s, phenyl).

EXAMPLE 8

Production of (3R,4R)-3-(N-benzyloxycarbonyl)methylamino-4-carboxymethyl-2-azetidinone [9]

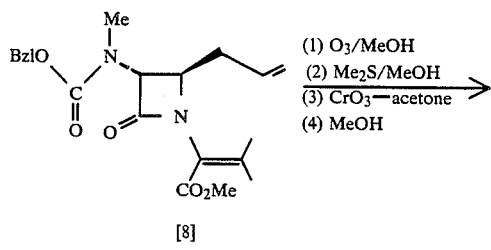

4.90 g (12.7 mmol) of (3R,4R)-3-(N-benzyloxycarbonyl)methylamino-1-(1-methoxycarbonyl-2-methyl-1-propenyl)-4-(2-propenyl)-2-azetidinone [8] was dissolved in 140 ml of methanol, and under cooling at −65° C., an ozone gas was blown into the solution for 4 hours. Then, nitrogen gas was blown into it to drive off the excess of the ozone gas. Dimethyl sulfide (4 ml) was added at −65° C., and the mixture was stirred overnight at room temperature.

The reaction mixture was concentrated under reduced pressure, and well dried under reduced pressure. The resulting syrup was dissolved in 50 ml of acetone, and 5.0 ml (13.4 mmol) of Jones reagent was added dropwise at 0° C. The reaction was carried out at 0° C. for 1 hour. Then, a small amount of 2-propanol was added, and the mixture was further stirred for 10 minutes.

The reaction mixture was concentrated to about 10 ml under reduced pressure, and then poured into ethyl acetate. The organic layer was successively washed with water and a saturated aqueous solution of sodium chloride, and dried over sodium sulfate.

The solvent was evaporated, and the resulting syrup was dissolved in 50 ml of methanol. The solution was heated at 60° C. for 5 hours. The reaction mixture was concentrated under reduced pressure, and the residue was dissolved in ethyl acetate, and acid components were extracted from it with a dilute aqueous solution of sodium hydrogen carbonate. The aqueous layer was adjusted to pH 2 with 4N hydrochloric acid, and extracted three times with ethyl acetate.

The organic layers were washed with a saturated aqueous solution of sodium chloride two times, and dried over sodium sulfate. The solvent was evaporated to give 2.73 g (74%) of the captioned compound as a colorless syrup.

IR $\nu_{max}^{CHCl_3}$ 3270, 1770, 1745, 1700cm$^{-1}$.

$^1$H NMR (CDCl$_3$) δ2.4–2.9 (2H, m, methylene), 2.99 (3H, s, NMe), 3.7–4.1 (1H, m, H-4), 4.85 (1H, bs, H-3), 5.13 (2H, s, benzyl), 7.2 (1H, bs, NH), 7.35 (5H, s, phenyl), 9.03 (1H, bs, COOH).

EXAMPLE 9

Production of (3R,4R)-3-(N-benzyloxycarbonyl)methylamino-4-(3-p-nitrobenzyloxycarbonyl-2-oxopropyl)-2-azetidinone [10]

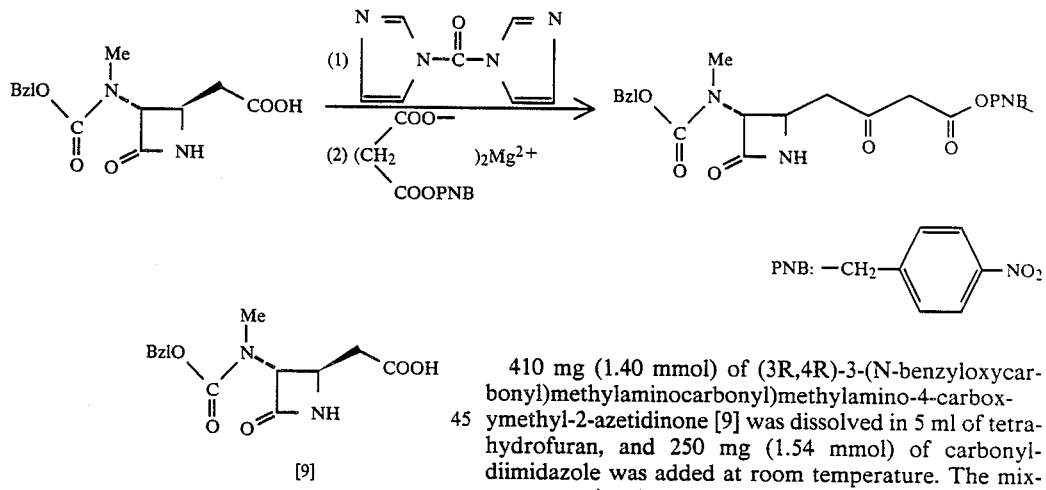

410 mg (1.40 mmol) of (3R,4R)-3-(N-benzyloxycarbonyl)methylaminocarbonyl)methylamino-4-carboxymethyl-2-azetidinone [9] was dissolved in 5 ml of tetrahydrofuran, and 250 mg (1.54 mmol) of carbonyldiimidazole was added at room temperature. The mixture was stirred at room temperature for 2 hours.

To the reaction mixture was added dropwise at room temperature 6 ml of a tetrahydrofuran solution of magnesium p-nitrobenzyl malonate prepared in tetrahydrofuran from 603 mg (2.52 mmol) of p-nitrobenzyl hydrogen malonate and 144 mg (1.26 mmol) of magnesium ethoxide.

The reaction mixture was stirred at room temperature for 10 minutes, and heated at 55° to 60° C. for 15 hours. The reaction mixture was diluted with ethyl acetate, washed successively with a cold 0.3N hydrochloric acid, a cold saturated aqueous solution of sodium hydrogen carbonate, and a saturated aqueous solution of sodium chloride, and dried over sodium sulfate.

The solvent was evaporated, and the resulting syrup was adsorbed on a column of silica gel (23 g) using methylene chloride. The column was eluted stepwise with benzene/acetone (10/1, 7/1, 5/1 and 3/1). Those fractions in the eluates which showed a UV absorption at an Rf of 0.35 in TLC developed with benzene/acetone (2/1) were collected and concentrated under reduced pressure to give 351 mg 53%) of the captioned compound as a colorless syrup.

IR $\nu_{max}^{CHCl_3}$ 3 3390, 1770, 1750 (shoulder), 1700, 1520, 1350 cm$^{-1}$.

$^1$H NMR (CDCl$_3$) δ2.70–3.15 (2H, m, C$_1'$ methylene), 2.99 (3H, s, NMe), 3.54 (2H, bs, C$_3'$ methylene), 3.91 (1H, m, H-4), 4.80 (1H, bs, H-3), 5.12 (2H, s, benzyl), 5.23 (2H, s, benzyl), 6.58 (1H, b, NH), 7.35 (5H, s, phenyl), 7.52 (2H, d, J=7 Hz, phenyl), 8.22 (2H, d, J=7 Hz, phenyl).

EXAMPLE 10

Production of (3R,4R)-3-(N-benzyloxycarbonyl)methylamino-4-(3-diazo-3-p-nitrobenzyloxycarbonyl-2-oxo)propyl-2-azetidinone [11]

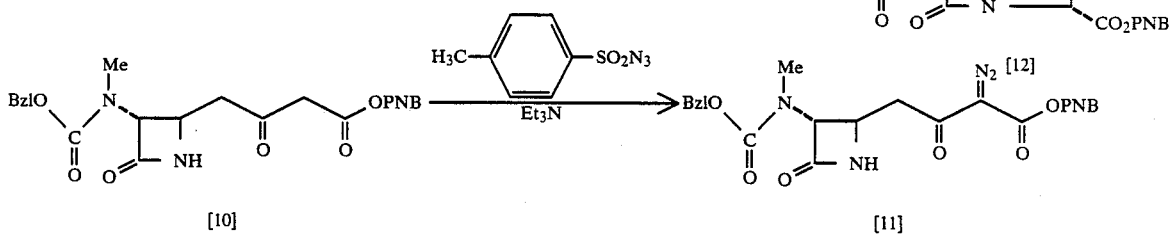

1.53 g (3.26 mmol) of (3R,4R)-3-(N-benzyloxycarbonyl)methylamino-4-(3-p-nitrobenzyloxycarbonyl-2-oxo)propyl-2-azetidinone [10] was dissolved in 12 ml of acetonitrile, and then 944 ml (4.89 mmol) of tosyl azide was added. To the solution was added dropwise 0.73 ml (5.24 mmol) of triethylamine at 0° C. The reaction mixture was stirred at 0° C. for 30 minutes and then at room temperature for 1.5 hours.

The reaction mixture was concentrated under reduced pressure, and the resulting syrup was adsorbed on a column of silica gel (70 g) using a small amount of methylene chloride. The column was eluted stepwise with benzene/acetone (10/1, 8/1, 6/1 and 4/1). Those fractions in the eluates which showed a UV absorption at an Rf of 0.56 in TLC developed with benzene/acetone (2/1) were collected and concentrated under reduced pressure to give 1.55 g (96%) of the captioned compound as a colorless foamable syrup.

IR $\nu_{max}^{CHCl_3}$ 3390, 2140, 1765. 1720 (shoulder), 1710, 1690 (shoulder), 1520, 1345cm$^{-1}$.

$^1$H NMR (CDCl$_3$) δ3.03 (3H, s, NMe), 3.10–3.70 (2H, m, methylene), 4.03 (1H, m, H-4), 4.93 (1H, bs, H-3), 5.20 (2H, s, benzyl), 5.42 (2H, s, benzyl), 6.72 (1H, b, NH), 7.43 (5H, s, phenyl), 7.62 (2H, d, J=8.5 Hz, phenyl), 8.33 (2H, d, J=8.5 Hz, phenyl).

EXAMPLE 11

Production of p-nitrobenzyl (2R,5R,6R)-6-(N-benzyloxycarbonyl)methylamino-3,7-dioxo-1-azabicyclo-[3.2.0]heptane-2-carboxylate [12]

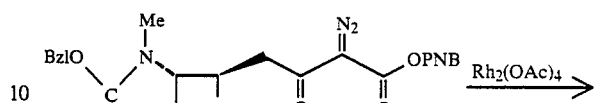

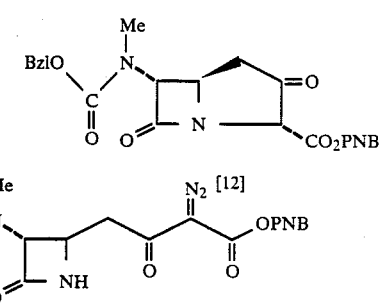

555 mg (1.12 mmol) of (3R,4R)-3-(N-benzyloxycarbonyl)methylamino-4-(3-diazo-3-p-nitrobenzyloxy carbonyl-2-oxo)propyl-2-azetidinone [11] was dissolved in 60 ml of benzene, and about 20 mg of rhodium acetate dimer was added. The mixture was heated under reflux for 40 minutes.

After the reaction mixture was allowed to cool, it was diluted with benzene, washed twice with a saturated aqueous solution of sodium chloride, and dried over sodium sulfate. The solvent was evaporated to give 524 mg (100%) of the captioned compound as a pale yellow foamable syrup.

IR $\nu_{max}$ $^{CHCl_3}$ 1770, 1750, 1735 (shoulder), 1695. 1520. 1345 cm$^{-1}$.

$^1$H NMR (CDCl$_3$) δ2.60–2.93 (2H, m, C$_4$ methylene), 3.13 (3H, s, NMe), 4.22 (1H, td, J=2.0 and 7.2 Hz, H-4), 4.84 (1H, s, H-2), 5.21 (2H, s, benzyl), 5.2–5.5 (1H, m, H-6), 5.34 (2H, bs, benzyl), 7.45 (5H, s, phenyl), 7.57 (2H, d, J=8 Hz, phenyl), 8.30 (2H, d, J=8 Hz, phenyl).

EXAMPLE 12

Production of p-nitrobenzyl (5R,6R)-3-(2-acetamidoethylthio)-6-(N-benzyloxycarbonyl)methylamino-7-oxo-1-azabicyclo[3.2.0]hept-2-ene-2-carboxylate [13]

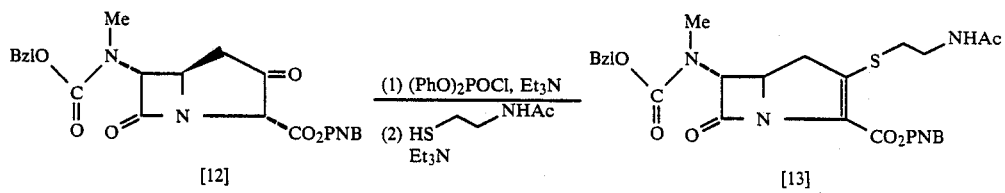

523 mg (1.12 mmol) of p-nitrobenzyl (2R,5R,6R)-6-(N-benzyloxycarbonyl)methylamino-3,7-dioxo-1-azabicyclo[3.2.0]heptane-2-carboxylate was dissolved in 8 ml of N,N-dimethylformamide, and under cooling at −50° C., 0.234 ml (1.68 mmol) of triethylamine, and;, then 0.279 ml (1.35 mmol) of diphenylphosphoryl chloride were added dropwise. The reaction solution was stirred at −50° C. for 40 minutes, and a DMF solution (2 ml) of 0.187 ml (1.34 mmol) of triethylamine and 200 mg (1.68 mmol) of N-acetylcysteamine was added dropwise at −50° C.

The mixture was stirred at −50° C. for 2 hours, and the reaction mixture was poured into methylene chloride, washed with cold 0.1M sodium phosphate buffer (pH 7.0) three times, and dried over sodium sulfate. The dried product was concentrated under reduced pressure to about 5 ml. The solution was adsorbed on a column of silica gel (25 g), and the column was eluted stepwise with benzene/acetone (5/1, 4/1 and 2/1).

Those fractions in the eluates which showed a UV absorption at an Rf of 0.58 in TLC developed with benzene/acetone (1/1) were collected and concentrated under reduced pressure to give 382 mg (60%) of the captioned compound as a colorless syrup.

IR $\nu_{max}^{CHCl_3}$ 3430, 1775, 1720 (shoulder), 1690, 1665, 1520, 1330 cm$^{-1}$.

$^1$H NMR (CDCl$_3$) δ2.00 (3H, s, NAc), 2.9–3.7 (6H, m, 3 x methylene), 3.09 (3H, s, NMe), 4.37 (1H, td, J=3.0 and 9.0 Hz, H-5), 5.24 (2H, s, benzyl), 5.2–5.4 (1H, m, H-6), 5.29 (1H, d, J=14 Hz

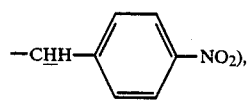

5.55 (1H, d, J=14 Hz

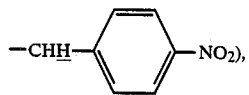

6.12 (1H, b, NH), 7.46 (5H, s, phenyl), 7.74 (2H, d, J=8 Hz, phenyl), 8.30 (2H, d, J=8 Hz, phenyl).

EXAMPLE 13

Production of sodium (5R,6R)-3-(2-acetamidoethylthio)-6-(N-benzyloxycarbonyl)methylamino-7-oxo-1-azabicyclo[3.2.0]hept-2-ene-2-carboxylate [14]

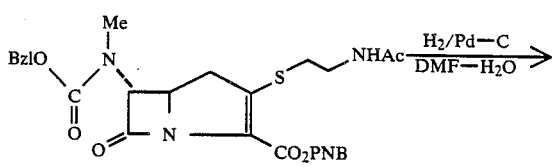

[13]

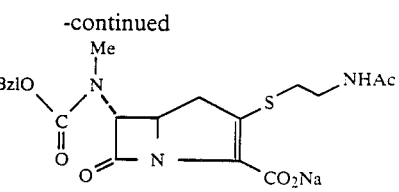

[14]

144 mg (0.25 mmol) of p-nitrobenzyl (5R,6R)-3-(2-acetamidoethylthio)-6-(N-benzyloxycarbonyl)methylamino-7-oxo-1-azabicyclo[3.2.0]hept-2-ene-2-carboxylate [13] was dissolved in 7 ml of N,N-dimethylformamide, and 5 ml of 0.1M sodium phosphate buffer (pH 7.8) and 100 mg of 10% palladium-carbon were added. The mixture was shaken for 1.5 hours in a Paar's device in a hydrogen tream under 4 atmosphere.

The catalyst was removed by filtration, and well washed with 0.01M sodium phosphate buffer (pH 7.4). The filtrate and the washing were combined, and 0.01M sodium phosphate buffer (pH 7.4) was added to adjust the total amount of the solution to 55 ml. The solution was adsorbed on a column of QAE Sephadex A-25 (25 ml) equilibrated with 0.01M sodium phosphate buffer (pH 7.4). The column was washed with 0.01M sodium phosphate buffer, and eluted with 0.01M sodium phosphate buffer (pH 7.4, 100 ml) and 0.4M aqueous sodium chloride (100 ml) by a linear concentration gradient method. Those fractions which had an absorption maximum at 303 nm on a UV spectrum were collected and 10 ml of 0.1M sodium phosphate buffer (pH 7.4) and 3.5 g of sodium chloride were added. The mixture was diluted with water to a total amount of 80 ml.

The solution was passed thorugh a column of Diaion CHP-20 (25 ml). The column was washed with water, and then eluted with water/a 50% aqueous 2-propanol solution by a linear concentration gradient method. Those fractions which had an absorption maximum at 303 nm on a UV spectrum were collected and lyophilized to give 66 mg (57%) of the captioned compound.

[α]$^{20}$ +54.5° (C 0.198, H$_2$O).

UV λ$_{max}^{H_2O}$ (ε): 303.5 nm (8,800).

IR λ$_{max}^{KBr}$ 1755, 1695, 1660, 1600 cm$^{-1}$ $^1$H NMR (D$_2$O, DSS internal standard) δ2.00 (3H, s, NAc), 2.8–3.3 (4H, m, 2 x methylene), 3.02 (3H, s, NMe), 3.40 (2H, t, J=6.6 Hz, methylene), 4.29 (1H, td, J=2.9 and 9.0 Hz, H-5), 5.07 (1H, d, J=2.9 Hz, H-6), 5.22 (2H, s, benzyl), 7.50 (5H, s, phenyl).

EXAMPLE 14

Production of (3R,4R)-3-(N-benzyloxycarbonyl)methylamino-4-methoxycarbonylmethyl-2-azetidinone [15]

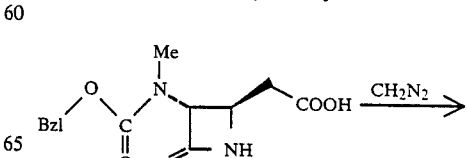

[9]

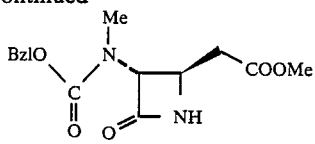

[15]

15.0 g (51.3 mmol) of (3R,4R)-3-(N-benzyloxycarbonyl)methylamino-4-carboxymethyl-2-azetidinone [9] (Example 8) was dissolved in 200 ml of methylene chloride, and a slightly excess of a diazomethane-ether solution (about 200 ml) was added at 0° C. The mixture was stirred at 0° C. for 2 hours.

The reaction mixture was concentrated under reduced pressure. The resulting syrup was dissolved in a small amount of methylene chloride, and adsorbed on a column of silica gel (400 g). The column was eluted stepwise with benzene/ethyl acetate (4/1, 2/1 and 1/1). Those fractions in the eluates which showed a UV absorption at an Rf of 0.30 in TLC developed with benzene/ethyl acetate (1/1) were collected, and concentrated under reduced pressure to give 13.1 g (83%) of the captioned compound.

$^1$H MMR (CDCl$_3$) δ2.6–3.0 (2H, m, methylene), 3.04 (3H, s, HMe), 3.75 (3H, s, CO$_2$CH$_3$), 3.8–4.15 (1H, m, H-4), 4.85 (1H, bs, H-3), 5.18 (2H, s, benzyl), 6.7–6.9 (1H, b, NH), 7.45 (5H, s, phenyl).

EXAMPLE 15

Production of (3R,4R)-3-(N-carbomethoxy-N-methyl)amino-4-methoxycarbonylmethyl-2-azetidinone [16]

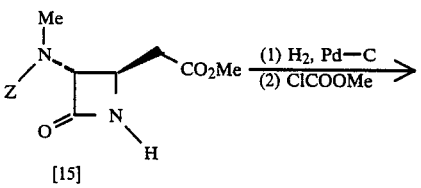

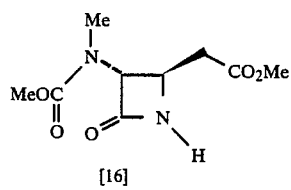

5.29 g (0.0176 mol) of (3R,4R)-3-(N-benzyloxycarbonyl-N-methyl)amino-4-methoxycarbonylmethyl-2-azetidinone [15] was dissolved in 40 ml of methanol, and 1.25 g of 10% palladium-carbon was added. The mixture was shaken for 3 hours under a hydrogen pressure of 4.5 kg/m$^2$.

The catalyst was separated from the reaction mixture by filtration, and the filtrate was concentrated under reduced pressure to form 2.84 g of an amine compound. The amine compound was dissolved in 50 ml of methylene chloride in an atmosphere of nitrogen, and under ice cooling, 1.99 ml (0.0259 mol) of methyl chloroformate and 4.34 ml (0.0311 mol) of triethylamine were added. The mixture was stirred for 15 minutes, and the disappearance of the raw material was determined by ninhydrin reaction.

The reaction mixture was concentrated under reduced pressure, and after adding ethyl acetate, the precipitated salt was separated by filtration. The filtrate was concentratrd under reduced pressure, and purified by a column of silica gel (300 g). Fractions eluted with benzene/acetone (1:1) were collected to obtain 1.70 g (yield 43%) of the captioned compound.

IR spectrum $\nu_{max}^{CHCl_3}$ cm$^{-1}$: 3420, 1780, 1740, 1710.

NMR spectrum (CDCl$_3$)δ$_{ppm}$: 2.80 (2H, m, C$_5$—H$_2$), 3.00 (3H, s, N—CH$_3$), 3.63 (6H, s, CO$_2$Mex2), 3.95 (1, m, C$_4$—H), 4.83 (1H, d, J=2.5 Hz, C$_3$—H), 7.35 (1H, br, —NH).

EXAMPLE 16

Production of (3R,4R)-3-(N-carbomethoxy-N-methyl)amino-4-carboxymethyl-2-azetidinone [17]

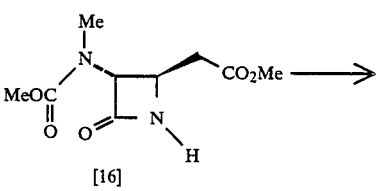

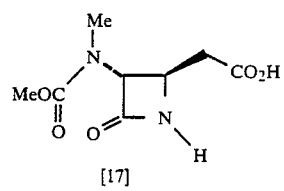

74 mg (0.32 mmol) of 3-(N-carbomethoxy-N-methyl)amino-4-methoxycarbonylmethyl-2-azetidinone [16] was dissolved in 0.65 ml of methanol and 0.32 ml of water, and at 0° C., 0.32 ml (0.32 mmol) of a 1N aqueous solution of sodium hydroxide was added. The mixture was reacted at the above temperature for 2 hours.

The reaction mixture was passed through a column of Amberlite CG-50 (H$^+$ form; 40 ml) washed with methanol using water as an eluent. Fractions which showed acidity were concentrated to dryness, and azeotropically distilled with chloroform to give 54 g (yield 78%) of the captioned compound which was foamable.

IR spectrum $\nu_{max}^{CHCl_3}$ cm$^{-1}$: 1770 (sh), 1745, 1702.

NMR spectrum (CDCl$_3$)δ$_{ppm}$: 2.68 (2H, d, J=8 Hz, C$_5$—H$_2$), 2.93 (3H, s, N—CH$_3$), 3.70 (3H, s, COOCH ), 3.95 (1H, dt, J=2.5 Hz and 8 Hz, C$_4$—H), 4.72 (1H, d, J=2.5 Hz, C$_3$—H).

EXAMPLE 17

Production of (3R,4R)-3-(N-carbomethoxy-N-methyl)amino-4-[3-(p-nitrobenzyloxycarbonyl)-2-oxopropyl]-2-azetidinone 18]

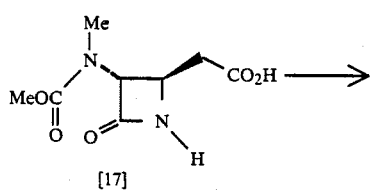

-continued

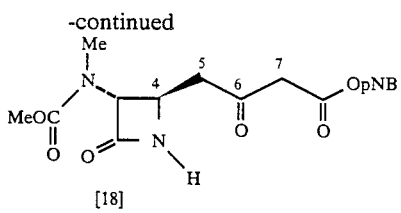

[18]

460 mg (2.13 mmol) of (3R,4R)-3-(N-carbomethoxy-N-methyl)amino-4-carboxymethyl-2-azetidinone [17] was dissolved in 10 ml of anhydrous THF, and 280 mg (2.34 mmol) of carbonyldiimidazole was added. The mixture was stirred at room temperature for 2 hours.

To the reaction mixture was added dropwise at room temperature 10 ml of an anhydrous THF solution of a magnesium salt prepared from 917 mg (3.83 mmol) of p-nitrobenzyl malonate and 219 mg (1.92 mmol) of magnesium ethoxide. The mixture was stirred at room temperature for 30 minutes and then reacted at 55° C. for 15 hours.

The reaction mixture was diluted with ethyl acetate, washed successively with cold 0.5N hydrochloric acid, a cold saturated aqueous solution of sodium hydrogen carbonate, and a saturated aqueous solution of sodium chloride, and dried over anhydrous sodium sulfate.

The dried product was concentrated under reduced pressure to remove the solvent. The resulting syrup was adsorbed on a column of silica gel (20 g) and eluted stepwise with benzene/acetone (10/1, 5/1, 3/1 and 2/1) to give 408 mg (yield 44%) of the captioned compound as a foamable syrup.

IR spectrum $\nu_{max}^{CHCl_3}$ cm$^{-1}$: 3400, 1770, 1710, 1605, 1520, 1350.

NMR spectrum (CDCl$_3$)$\delta_{ppm}$: 2.95 (3H, s, N—CH$_3$), 3.06 (2H, m, C$_5$—H$_2$), 3.62 (2H, s, C$_7$—H$_2$), 3.71 (3H, s, CO$_2$CH$_3$), 3.93 (1H, m, C$_4$—H), 4.78 (1H, d, J=2.5 Hz, C$_3$—H), 5.28 (2H, s, CO$_2$CH$_2$—Ar), 6.61 (1H, br, NH), 7.52 (2H, d, J=9.0 Hz, Ar), 8.22 (2H, d, J=9.0 Hz, Ar).

EXAMPLE 18

Production of (3R,4R)-2-(N-carbomethoxy-N-methyl)amino-4-[3-(p-nitrobenzyloxycarbonyl)-2-oxo-3-diazopropyl]-2-azetidinone [19]

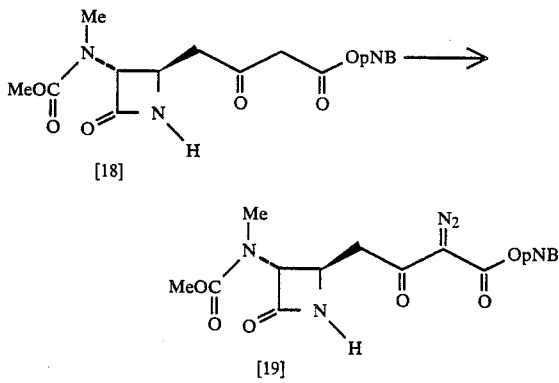

222 mg (0.51 mmol) of (3R,4R)-3-(N-carbomethoxy-N-methyl)amino-4[3-(p-nitrobenzyloxycarbonyl)-2-oxopropyl]-2-azetidinone [18] was dissolved in 2 ml of acetonitrile, and the solution was cooled with ice in a stream of nitrogen. 114 microliters (0.82 mmol) of triethylamine and 151 mg (0.77 mmol) of p-toluenesulfonylazide were added. The mixture was stirred for 10 minutes at the above temperature, and then for 1.5 hours at room temperature.

The reaction mixture was concentrated under reduced pressure, and adsorbed onto a column of silica gel (10 g). The column was eluted stepwise with benzene/acetone (10/1, 5/1, 3/1 and 2/1) to give 220 mg (yield 94%) of the captioned compound as a foamable syrup.

IR spectrum $\nu_{max}^{CHCl_3}$ cm$^{-1}$: 3400, 2280, 1765, 1705, 1645, 1605 1520.

NMR spectrum (CDCl$_3$)$\delta_{ppm}$: 2.96 (3H, s, N—CH$_3$), 3.33 (2H, m, C$_5$—H$_2$), 3.98 (1H, m, C$_4$—H), 4.85 (1H, d, J=2.5 Hz, C$_3$—H), 5.38 (2H, s, O—CH$_2$-Ar), 6.78 (1H, br, N—H), 7.56 (2H, d, J=9.0 Hz, Ar), 8.24 (2H, d, J=9.0 Hz, Ar).

EXAMPLE 19

Production of (5R,6R)-p-nitrobenzyl 6-(N-carbomethoxy-N-methyl)amino-1-azabicyclo[3.2.0]heptane-3,7-dione-2-carboxylate [20]

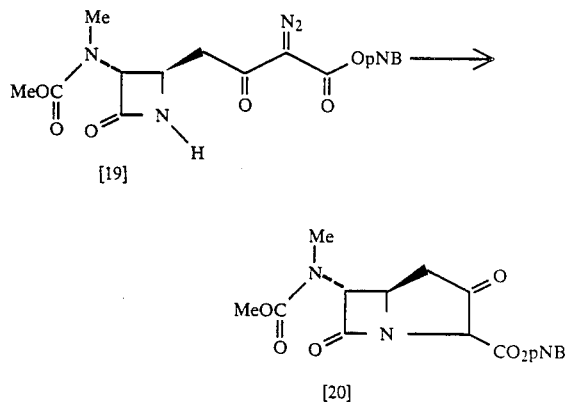

304 mg (0.0725 mmol) of (3R,4R)-3-(N-carbomethoxy-N-methyl)amino-4-[3-(p-nitrobenzyloxycarbonyl)-2-oxo-3-diazopropyl]-2-azetidinone [19] was dissolved in 30 ml of benzene. A small amount of rhodium acetate dimer was added, and the solution was deaerated and refluxed for 20 minutes.

The reaction mixture was air-cooled and 30 ml of benzene was added. The mixture was washed with 20 ml of water twice, dried over anhydrous sodium sulfate, and concentrated under reduced pressure to remove the solvent and give 234.5 mg (yield 82%) of the captioned compound.

IR spectrum $\nu_{max}^{CHCl_3}$ cm$^{-1}$: 1770, 1750, 1700, 1610.

NMR spectrum (CDCl$_3$)$\delta_{ppm}$: 2.79 (2H, d, J=7 Hz, C$_4$—H$_2$), 3.02 (3H, s, N—CH$_3$), 3.70 (3H, s, CH$_3$OCO-N), 4.18 (1H, brt, J=7 Hz, C$_5$—H), 4.80 (1H, s, C$_2$—H), 5.0-5.4 (3H, br, OCH$_2$-Ar and C$_6$—H), 7.50 (2H, d, J=9 Hz, Ar), 8.17 (2H, d, J=9 Hz, Ar).

EXAMPLE 20

Production of (5R,6R)-p-nitrobenzyl 6-(N-carbomethoxy-N-methyl)amino-3-acetamidoethylthio-1-azabicyclo[3.2.0]hept-2-ene-7-one-2-carboxylate [21]

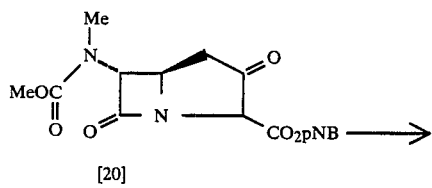

[20]

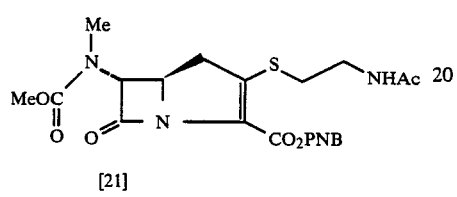

[21]

228 mg (0.527 mmol) of (5R,6R)-p-nitrobenzyl 6-(N-carbomethoxy-N-methyl)amino-1-azabicyclo[3.2.0]heptane-3,7-dione-2-carboxylate [20] was dissolved in 5 ml of anhydrous dimethylformamide. The solution was cooled to −50° C., and 110 microliters (0.790 mmol) of triethylamine and 131.6 microliters (0.632 mmol) of diphenylphosphoryl chloride were added dropwise, and the mixture was stirred at the above temperature for 1 hour. Furthermore, 1 ml of a dimethylformamide solution of 88.3 microliters (0.632 mmol) of triethylamine and 94 mg (0.79 mmol) of N-acetylcysteamine was added dropwise.

The mixture was stirred at the above temperature for 2 hours, and then for 30 minutes at 0° C. The reaction mixture was diluted with methylene chloride, washed with 0.1M phosphate buffer (pH 7.0) three times, dried over anhydrous sodium sulfate, and concentrated under reduced pressure.

The residue was adsorbed on a column of silica gel (10 g). The column was eluted stepwise with benzene/acetone (5/1, 3/1, 2/1, 1/1 and 1/2) to give 222 mg (yield 78%) of the captioned compound.

Specific rotation $[\alpha]_D^{23}$: +31.7° (c 0.5, $CH_2Cl_2$)

UV spectrum $\lambda_{max}^{CH_2Cl_2}$ nm($\epsilon$): 271 (12900), 321 (13800).

IR spectrum $\nu_{max}$CHCl$_3$ cm$^{-1}$: 1780, 1700.

NMR spectrum (CDCl$_3$)$\delta_{ppm}$: 1.97 (3H, s, NHCOC$\underline{H}_3$), 2.70-3.60 (m, 6H, C$_4$—H$_2$ and S—C$\underline{H}_2$—CH$_2$—N), 3.00 (3$\overline{H}$, s, N—CH$_3$), 3.74 (3H, s, CH$_3$O—CO—N), 4.28 (1$\overline{H}$, dt, J=3.0 Hz and 9.$\overline{0}$ Hz, C$_5$—H), 5.20 (1H, d, J=14.0 Hz, OCH$\underline{H}$—Ar), 5.21 (1H, br, C$_6$—H), 5.45 (1H, d, J=14.0 Hz, OC$\underline{H}$H—Ar), 6.18 (1H, br, NHAc), 7.62 (2H, d, J=9.0 Hz, Ar), 8.20 (1H, d, J=9.0 Hz, Ar).

EXAMPLE 21

Production of sodium (4R,5R)-6-(N-carbomethoxy-N-methyl)amino-3-acetamidoethylthio-1-azabicyclo[3.2.0]hept-2-ene-7-one-2-carboxylate [22]

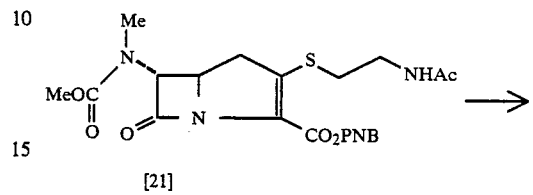

[21]

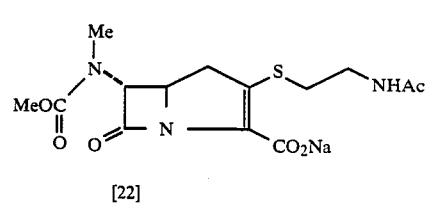

[22]

190 mg of (4R,5R)-p-nitrobenzyl 6-(N-carbomethoxy-N-methyl)amino-3-acetamidoethylthio-1-azabicyclo[3.2.0]hept-2-ene-7-one-2-carboxylate [21] was dissolved in 9.5 ml of tetrahydrofuran, and 9.5 ml of 0.1M phosphate buffer (pH 7.38) was added. Platinum oxide (190 mg) was added, and the mixture was shaken for 3.5 hours under a hydrogen pressure of 4.5 atmospheres. The catalyst was separated by filtration using Celite. The filtrate was concentrated under reduced pressure to one-half of the original volume, and again filtered through Celite.

The filtrate was adsorbed on a column of QAE Sephadex A-25 (20 ml) equilibrated with 0.01M phosphate buffer (pH 7.4). The column was eluted with a 0-5% aqueous solution of sodium chloride (80 ml, 80 ml) by a linear gradient method.

Fractions which showed activity in a UV spectrum (maximum wavelength about 303 nm) and in bioassay were collected (60 ml), and 3 g of sodium chloride was added. The mixture was adsorbed on a column of Diaion CHP-20 (20 ml). The column was washed with water, and then eluted with a 0-50% aqueous solution of isopropanol. Fractions which showed a UV absorption at 303.5 nm were lyophilized to give 57.2 mg (yield 41%) of the captioned compound as a pale yellow powder.

Specific rotation $[\alpha]_D^{23}$: +45.2° (c 0.25, H$_2$O ).

UV spectrum $\lambda_{max}^{H_2O}$ nm($\epsilon$): 303.5 (10600).

IR spectrum $\nu_{max}^{KBr}$ cm$^{-1}$: 1760, 1700 1660, 1600.

NMR spectrum (D$_2$O, DSS)$\delta_{ppm}$: 2.00 (3H, s, NHCOC$\underline{H}_3$), 2.70-3.45 (6H, m, C$_4$-H$_2$ and —S—C$\underline{H}_2$—C$\underline{H}_2$—N—), 3.00 (3H, s, N—CH$_3$), 3.76 (3H, s, CH$_3$OCO), 4.35 (1H, dt, J=3.0 Hz and 9.0 Hz, C$_5$—H), 5.12 (1H, d, J=3.0 Hz, C$_6$—H).

EXAMPLE 22

Production of (3R,4R)-3-(N-methanesulfonyl)methylamino-4-methoxycarbonylmethyl-2-azetidinone [23]

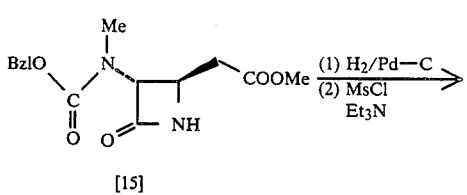

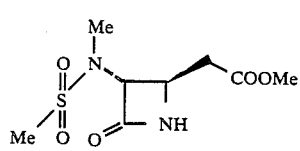

430 mg (1.40 mmol) of (3R,4R)-3-(N-benzyloxycarbonyl)methylamino-4-methoxycarbonylmethyl-2-azetidinone [15] was dissolved in 8 ml of methanol, and 100 mg of 10% palladium-carbon was added. The mixture was shaken at room temperature for 3 hours in a hydrogen current under a pressure of 4 atmospheres in a Paar's device.

The catalyst was removed by filtration and well washed with methanol. The filtrate and the washing were combined, and concentrated under reduced pressure to give a colorless syrup.

The syrup was dissolved in 4 ml of methylene chloride, and with stirring at 0° C., 0.293 ml (2.10 mmol) of triethylamine and then 0.13 ml (1.68 mmol) of methanesulfonyl chloride were added dropwise, and the mixture was reacted at 0° C. for 1 hour and then at 5° C. for 16 hours.

While the reaction mixture was stirred at 0° C., 30 microliters of methanol was added. The mixture was stirred for 30 minutes, and then concentrated under reduced pressure. The residue was suspended in a small amount of methylene chloride and adsorbed on a column of silica gel (10 g). The column was eluted stepwise with benzene/acetone (5/1, 3/1 and 2/1). Those fractions in the eluates which showed iodine coloration at an Rf of 0.36 in TLC developed with benzene-acetone (2:1) were collected and concentrated under reduced pressure to give mg (70%) of the captioned compound.

IR $\nu_{max}^{KBr}$ 3220, 1735, 1710, 1320, 1150 cm$^{-1}$ $^1$H NMR (CDCl$_3$) $\delta$2.64 (1H, dd, J=9.0 and 16.8 Hz, —CHH—CO$_2$Me), 2.95 (1H, dd, J=4.5 and 16.8 Hz, —CHH—CO$_2$Me), 2.98 (3H, s, NMe or NMs), 3.03 (3H, s, NMs or NMe), 3.75 (3H, s, CO$_2$CH$_3$), 4.03 (1H, ddd, J=2.7, 4.5 and 9.0 Hz, H-4), 4.70 (1H, d, J=2.7 Hz, H-3), 6.77 (1H, bs, NH).

EXAMPLE 23

Production of (3R,4R)-4-carboxymethyl-3-(N-methanesulfonyl)methylamino-2-azetidinone [24]

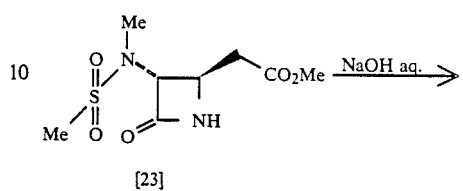

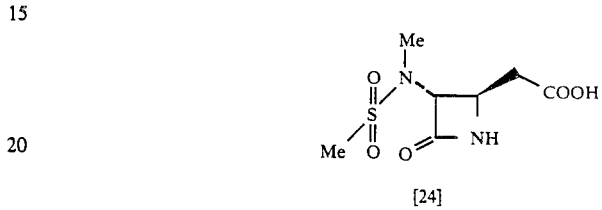

1.79 g (7.15 mmol) of (3R,4R)-3-(N-methanesulfonyl)methylamino-4-methoxycarbonylmethyl-2-azetidino [23] was dissolved in 16 ml of methanol and 7.5 ml of water. With stirring at 0° C., 7.1 ml of a 1N aqueous solution of sodium hydroxide was added dropwise, and the mixture was stirred at 0° C. for 2.5 hours.

About 10 ml of Amberlite CG-50 (H$^+$ form) was added to the reaction mixture, and the mixture was stirred for 30 minutes. Then, the reaction mixture was diluted with water to adjust its total amount to 80 ml, and passed through a column of Amberlite CG-50 (H$^+$ form) (100 ml). The column was washed with water. Those fractions in the eluates which showed acidity (pH 3–4) were collected and concentrated under reduced pressure to give a solid residue.

The residue was recrystallized from methanol, and methylene chloride was added. The crystals were collected by filtration to give 975 mg (58%) of the captioned compound.

IR $\nu_{max}^{KBr}$ 3450, 1740, 1700, 1335, 1150 cm$^{-1}$.

$^1$H NMR (MeOH-d$_4$) $\delta$2.5–2.9 (2H, m, methylene), 2.96 (3H, s, NMe or NMs), 3.03 (3H, s, NMs or NMe), 4.07 (1H, m, H-4). (H-3 was hidden by the peak of HDO and could not be detected.)

EXAMPLE 24

Production of (3R,4R)-2-(N-methanesulfonyl)methylamino-4-(3-p-nitrobenzyloxycarbonyl-2-oxopropyl)-2-azetidinone [25]

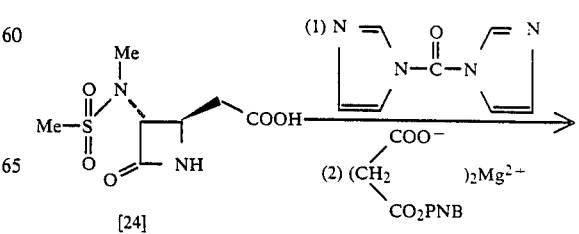

-continued

[Structure [25]: azetidinone with N-Me, SO2Me, NH, and side chain -CH2-C(=O)-CH2-C(=O)-OPNB]

[25]

800 mg (3.39 mmol) of (3R,4R)-4-carboxymethyl-3-(N-methanesulfonyl)methylamino-2-azetidinone [24] was suspended in 9 ml of tetrahydrofuran, and 604 mg (3.72 mmol) of 1,1-carbonyldiimidazole was added. The mixture was stirred at room temperature for 2 hours.

A tetrahydrofuran solution (12 ml) of magnesium p-nitrobenzylmalonate obtained by stirring 1.30 g (5.44 mmol) of p-nitrobenzyl hydrogen malonate and 310 mg (2.71 mmol) of magnesium ethoxide in 20 ml of tetrahydrofuran at room temperature for 4 hours, and drying the resulting product was added to the above reaction mixture. The mixture was stirred at room temperature for 10 minutes, and then at 45° to 50° C. for 16 hours.

The reaction mixture was concentrated under reduced pressure to about 3 ml, diluted with ethyl acetate, washed successively with a 0.5N aqueous solution of hydrochloric acid, a saturated aqueous solution of sodium bicarbonate, water and a saturated aqueous solution of sodium chloride, and dried over sodium sulfate.

The solvent was evaporated. The resulting syrup was dissolved in a small amount of methylene chloride and adsorbed on a column of silica gel (40 g). The column was eluted stepwise with benzene/acetone (5/1, 3/1 and 2/1). Those fractions in the eluates which showed a UV absorption at an Rf of 0.56 in TLC developed with benzene/acetone (1/1) were collected and concentrated under reduced pressure to give 806 mg (58%) of the captioned compound.

IR $\nu_{max}$ $^{CHCl_3}$: 3390, 1765, 1740 (shoulder), 1715, 1520, 1345, 1150 cm$^{-1}$.

$^1$H NMR (CDCl$_3$) δ2.82 (1H, dd, J=9.2 and 18.0 Hz,

[fragment structure: N—CHH—C(=O)]

), 2.96 (3H, s, NMe or NMs), 3.00 (3H, s, NMs or NMe), 3.25 (1H, dd, J=4.4 and 18.0 Hz,

[fragment structure: N—CHH—C(=O)]

), 3.62 (2H, s,

[fragment: C(=O)—CH2—CO2PNB]

), 4.01 (1H, ddd, J=2.6, 4.4 and 9.2 Hz, H-4), 4.63 (1H, d, J=2.6 Hz, H-3), 5.27 (2H, s, benzyl), 6.45 (1H, b, NH), 7.55 (2H, d, J=9 Hz, phenyl), 8.25 (2H, d, J=9 Hz, phenyl).

EXAMPLE 25

Production of (3R,4R)-4-(3-diazo-3-p-nitrobenzyloxycarbonyl-2-oxopropyl)-3-(N-methanesulfonyl)methylamino-2-azetidinone [26]

[Structure [25] → TsN3/Et3N → Structure [26] with N2 diazo group]

[25]

[26]

848 mg (2.05 mmol) of (3R,4R)-3-(N-methanesulfonyl)methylamino-4-(3-p-nitrobenzyloxycarbonyl-2-oxopropyl)-2-azetidinone [25] was dissolved in 7 ml of acetonitrile, and an acetonitrile solution (3 ml) of 607 mg (3.08 mmol) of tosyl azide was added. While the reaction mixture was stirred with ice cooling, 0.46 ml (3.30 mmol) of triethylamine was added dropwise. The mixture was stirred at 0° C. for 30 minutes and then at room temperature for 1.5 hours.

The reaction mixture was concentrated under reduced pressure. The resulting oil was adsorbed on a column of silica gel (30 g) using a small amount of methylene chloride. The column was eluted stepwise with benzene/acetone (8/1, 6/1, 4/1 and 2/1). Those fractions in the eluates which showed a UV absorption at an Rf of 0.64 in TLC developed with benzene/acetone (1/1) were collected and concentrated under reduced pressure to give mg (81%) of the captioned compound.

IR $\nu_{max}$ $^{CHCl_3}$: 3400, 2150, 1770, 1720, 1650, 1525, 1350, 1155 cm$^{-1}$.

$^1$H NMR (CDCl$_3$) δ2.97 (3H, s, NMe or NMs), 3.02 (3H, s, NMs or NMe), 3.08 (1H, dd, J=9.0 and 17.6 Hz, —CHH—), 3.58 (1H, dd, J=3.9 and 17.6 Hz, —CHH—), 4.06 (1H, ddd, J=2.7, 3.9 and 9.0 Hz, H-4), 4.73 (1H, d, J=2.7 Hz, H-3), 5.40 (2H, s, benzyl), 6.56 (1H, bs, NH), 7.58 (2H, d, J=9 Hz, phenyl), 8.28 (2H, d, J=9 Hz, phenyl).

EXAMPLE 26

Production of p-nitrobenzyl (2R,5R,6R)-3,7-dioxo-6-(N-methanesulfonyl)methylamino-1-azabicyclo[3.2.0]heptane-2-carboxylate [27]

[Structure [26] → Rh2(OAc)4/PhH →]

[26]

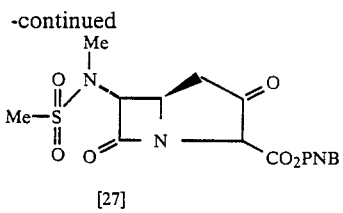

[27]

600 mg (1.37 mmol) of (3R,4R)-4-(3-diazo-3-p-nitrobenzyloxycarbonyl-2-oxopropyl)-3-(N-methylamino-2-azetidinone [26] was suspended in 60 ml of benzene, and about 30 mg of rhodium acetate dimer was added. The mixture was heated under reflux for 50 minutes.

The reaction mixture was allowed to cool, diluted with benzene, washed with a saturated aqueous solution of sodium chloride twice, and dried over sodium sulfate. The solvent was evaporated to give 503 mg (90%) of the captioned compound as a solid residue.

IR $\nu_{max}^{KBr}$ 1760, 1740, 1510, 1340, 1145 cm$^{-1}$.

$^1$H NMR (DMF-d$_7$, TMS internal standard) δ3.09 (3H, s, NMe or NMs), 3.13 (3H, s, NMs or NMe), 3.2–3.6 (2H, m, methylene), 4.55 (1H, td, J=2.7 and 72. Hz, H-5), 4.98 (1H, s, H-2), 5.32 (1H, d, J=2.7 Hz, H-6), 5.47 (2H, s, benzyl), 7.79 (2H, d, J=9 Hz, phenyl), 8.35 (2H, d, J=9 Hz, phenyl).

EXAMPLE 27

Production of p-nitrobenzyl (5R,6R)-3-(2-acetamidoethylthio)-6-(N-methanesulfonyl)methylamino-7-oxo-1-azabicyclo[3.2.0]hept-2-ene-2-carboxylate [28]

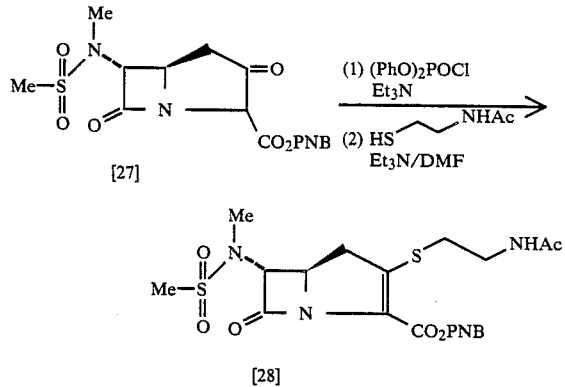

502 mg (1.22 mmol) of p-nitrobenzyl (2R,5R,6R)-3,7-dioxo-6-(N-methanesulfonyl)methylamino-1-azabicyclo[3.2.0]heptane-2-carboxylate [27] was dissolved in 4 ml of N,N-dimethylformamide, and with stirring at −30° to −40° C., 0.256 ml (1.84 mmol) of triethylamine and then 0.304 ml (1.47 mmol) of diphenylphosphoryl chloride were slowly added dropwise. The mixture was stirred at −30° to −40° C. for 1 hour. Then, an N,N-dimethylformamide solution (2.7 ml) of 233 mg (1.95 mmol) of N-acetylcysteamine and 0.221 ml (1.59 mmol) of triethylamine was added dropwise slowly, and the mixture was stirred at −35° C. for 1.5 hours. The reaction mixture was poured into methylene chloride, and washed with 0.1M phosphate buffer (pH 7.0) three times and a saturated aqueous solution of sodium chloride once, and dried over sodium sulfate. The product was carefully concentrated under reduced pressure to remove the solvent. When the amount of the residue reached about 5 ml, crystals precipitated. Ether was added, and the precipitated crystals were collected by filtration. The crystals were washed with methylene chloride/ether (1/1) to give 344 mg (55%) of the captioned compound as pale yellow crystals.

Melting point: 172°–175° C. (decomp.)

UV $\lambda_{max}^{CH_2Cl_2}$ nm(ε): 272 (12000), 323 (12700).

IR $\nu_{max}^{CHCl_3}$ 3420, 1775, 1670, 1515, 1340, 1150 cm$^{-1}$.

$^1$H NMR (CDCl$_3$) δ1.98 (3H, s, NAc), 3.01 (6H, s, NMe and NMs), 2.8–3.1 (2H, m, methylene), 3.25–3.60 (4H, m, methylene x 2), 4.37 (1H, td, J=2.9 and 9.2 Hz, H-5), 5.06 (1H, d, J=2.9 Hz, H-6), 5.23 (1H, d, J=13.2 Hz,

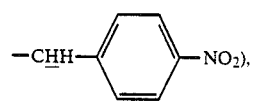

5.51 (1H, d, J=13.2 Hz,

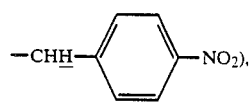

6.18 (1H, bt, J~6 Hz, NH), 7.66 (2H, d, J=9 Hz, phenyl), 8.25 (2H, d, J=9 Hz, phenyl).

EXAMPLE 28

Production of sodium (5R,6R)-3-(2-acetamidoethylthio)-6-(N-methanesulfonyl)methylamino-7-oxo-1-azabicyclo[3.2.0]hept-2-ene-2-carboxylate [29]

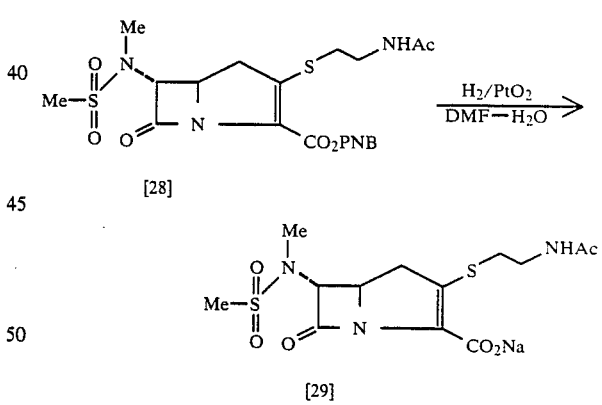

153 mg (0.298 mmol) of (5R,6R)-3-(2-acetamidoethylthio)-6-(N-methanesulfonyl)methylamino-7-oxo-1-azabicyclo[3.2.0]hept-2-ene-2-carboxylate [28] was dissolved in 10 ml of N,N-dimethylformamide, and 5 ml of 0.1M sodium phosphate buffer (pH 7.8) and 120 mg of platinum oxide were added. By using a Paar's device, the mixture was shaken at room temperature for 1 hour in a hydrogen stream under a pressure of 4 atmospheres. Five milliliters of 0.1M sodium phosphate buffer and 30 mg of platinum oxide were newly added, and the mixture was shaken further for 1.5 hours at room temperature in a hydrogen current under a pressure of 4 atmospheres.

To the reaction mixture was added 5 ml of 0.01M phosphate buffer (pH 7.4), and the catalyst was separated by filtration and washed well with the above solution. 0.01M phosphate buffer (pH 7.4) was added to the filtrate to adjust the total amount of the solution to 90 ml. It was passed through a column of QAE-Sephadex A-25 (22 ml) equilibrated with 0.01M phosphate buffer (pH 7.4).

The column was washed with 20 ml of 0.01M phosphate buffer (pH 7.4) and eluted with 0.01M phosphate buffer (pH 7.4) - 0.4M aqueous sodium chloride solution by a linear concentration gradiaent method. Those fractions in the eluates which showed an absorption maximum near 305 nm on a UV spectrum were collected, and 16 ml of 0.1M phosphate buffer (pH 7.4) and 4.5 g of sodium chloride were added. Water was added to adjust the total amount of the solution to 100 ml.

The solution was passed through a column of Diaion CHP-20 (20 ml). The column was washed with water, and then eluted with water/a 50% aqueous solution of 2-propanol by a linear concentration gradient method. Those fractions in the eluates which had an absorption maximum at 305 nm on a UV spectrum were collected and lyophilized to obtain 46 mg (38%) of the captioned compound as a white solid.

$[\alpha]_D^{21}$ +64.2° (c 0.123, H$_2$O )
UV $\epsilon_{max}^{H2O}$ nm($\epsilon$): 305 (8300).
IR $\nu_{max}^{KBr}$ 3360, 1755, 1660, 1595, 1330, 1150 cm$^{-1}$
$^1$H NMR (D$_2$O, DSS internal standard) δ1.98 (3H, s, NAc), 3.00 (3H, s, NMe or NMs), 3.12 (3H, s, NMs or NMe), 2.75-3.50 (6H, m, methylene x 3), 4.43 (1H, td, J=2.7 and 9.0 Hz, H-5), 5.11 (1H, d, J=2.7 Hz, H-6).
$^{13}$C NMR (D$_2$O, DSS internal standard) 24.4 (q,

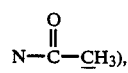

33.3 (t, —S—CH$_2$—CH$_2$-NHAc), 34.3 (q, N—CH ), 39.6 (q, N—SO$_2$CH$_3$), 40.2 (t, C-4 or —S—CH$_2$—CH$_2$—NHAc), 42.0 (t, C-4 or —S—CH$_3$—CH$_2$—NHAc), 58.9 (d, C-5), 71.8 (d, C-6), 129.8 (s, C-3 or C-2), 141.3 (s, C-3 or C-2), 170.4 (s, —CO$_2$Na), 176.2 (s,

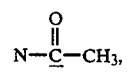

or C-7), 176.8 (s,

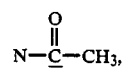

or C-7).

EXAMPLE 29

Production of (3R,4R)-3-dimethylamino-4-methoxycarbonylmethyl-2-azetidinone [30]

(1) Methylation with diazomethane

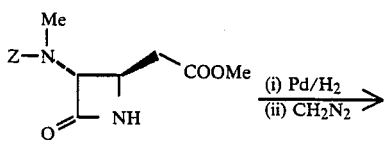

[15]

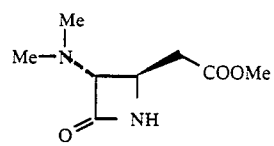

[30]

Five grams (0.016 mol) of (3R,4R)-3-(N-benzyloxycarbonyl-N-methyl)amino-4-methoxycarbonylmethyl-2azetidinone [15] was dissolved in 80 ml of methanol, and after adding 1.4 g of 10% palladium-carbon, catalytically reduced at room temperature under a pressure of 4 atmospheres for 4 hours. The catalyst was separated by filtration. The filtrate was concentrated under reduced pressure to obtain an amine compound. The amine compound was dissolved in 150 ml of methanol, and with ice cooling, 150 ml of an ether solution of diazomethane was added, and the reaction was carried out at the same temperature for 4 hours. The reaction mixtrue was concentrated under reduced pressure. The residue was dissolved in ethyl acetate, and the insoluble materials were removed by filtration. The mother liquor was adsorbed on a column of silica gel. The column was eluted stepwise with ethyl acetate/methanol (5/1 and 3/1). Those fractions in the eluates which showed iodine coloration at an Rf of 0.48 by silica gel TLC developed with ethyl acetate/methanol (3/1) were collected and concentrated under reduced pressure to give 859 mg of the captioned compound [30]. 647 mg of a methylamino compound having an Rf of 0.36 was recovered.

NMR (CDCl$_2$) δ: 2.40 (6H, s,

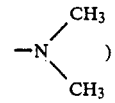

2.53 (1H, dd, J=9.0 and 16.0 Hz, CHH—COO) 2.78 (1H, dd, J=4.5 and 16.0 Hz, CHH—COO) 3.53 (1H, d, J=1.5 Hz, H-3) 3.72 (3H, s, OMe), 3.90 (1H, m, H-4) 6.53 (1H, br, NH).

(2) Methylation with methyl iodide

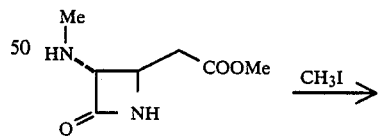

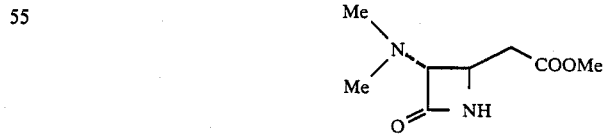

304 mg (1.76 mmol) of the methylamino compound recovered in (1) above was dissolved in 6 ml of methanol, and 491 microliters (3.53 mmol) of triethylamine and 220 microliters (3.53 mmol) of methyl iodide were added. The mixture was reacted at room temperature for 15 hours. The reaction mixture was concentrated under reduced pressure, and purified by a silia gel column to give 113 mg of the captioned compound.

EXAMPLE 30

Production of (3R,4R)-4-carboxymethyl-3-dimethylamino-2-azetidinone hydrochloride [31]

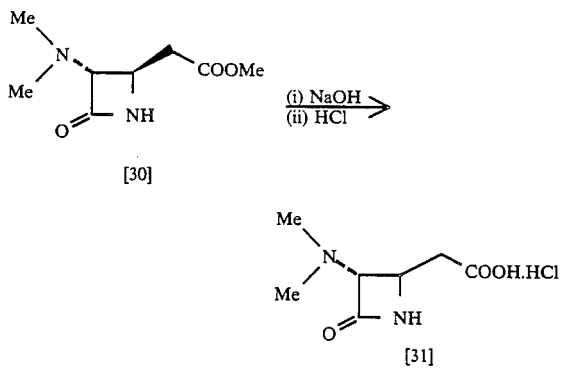

68 mg (0.365 mmol) of (3R,4R)-3-dimethylamino-4-methoxycarbonylmethyl-2-azetidinone [30] was dissolved in 3.6 ml of methanol. The solution was cooled to 0° C., and 3.6 ml of 0.1N sodium hydroxide was added. The mixture was reacted at the same temperature for 2 hours. To the reaction mixture was added 3 ml of IRC-CG50 (H+). The mixture was stirred for 1 hour, and passed through 10 ml of CG50 (H+). The solution that passed through it was dried under reduced pressure to give 51 mg (yield 82%) of a free form of the captioned compound. The free compound was dissolved in 1 ml of water, and under ice cooling, 2.7 ml of 0.1N HCl as added. The mixture was dried under reduced pressure to give its hydrochloride.

δ: 2.91 (2H, m, C$\underline{H}_2$—COOH), 3.10 (6H, s,

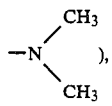

), 4.30 (1H, dt, J=2.5 and 7.0 Hz, H-4), 4.55 (1H, d, J=2.5 Hz, H-3).

EXAMPLE 31

Production of (3R,4R)-3-dimethylamino-4-(3-p-nitrobenzyloxycarbonyl-2-oxopropyl)-2-azetidinone [32]

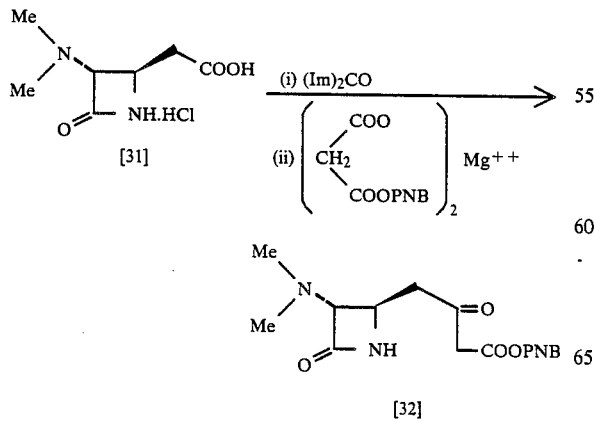

105 mg (0.5 mmol) of (3R,4R)-4-carboxymethyl-3-dimethylamino-2-azetidinone hydrochloride [31] was dissolved in 2 ml of dimethylformamide, and at room temperature, 98 mg (0.6 mmol) of carbonyldiimidazole was added. The mixture was reacted at the above temperarture for 2 hours.

Two milliliters of a dimethylformamide solution of magnesium p-nitrobenzylmalonate obtained by stirring mg (1 mmol) of p-nitrobenzyl hydrogen malonate and 58 mg (0.5 mmol) of magnesium ethoxide in 10 ml of tetrahydrofuran at room temperature for 15 hours and then drying the product was added to the reaction mixture obtained. The mixture was reacted at 50° C. for 15 hours. The reaction mixture was poured into 100 ml of ethyl acetate, and washed with an aqueous solution of sodium hydrogen carbonate. The washings were combined and extracted with ethyl cetate. The extract was washed with a saturated aqueous solution of sodium chloride, and dried over anhydrous sodium sulfate. The solvent was evaporated, and the residue was dissolved in a small amount of ethyl acetate, and adsorbed on four silica gel plates (20×20 cm) and developed with a mixture of ethyl acetate and methanol (3/1). Fractions having a UV absorption at an Rf of 0.52 were collected to give 23 mg of the captioned compound.

$\nu_{max}^{CHCl_3}$ cm$^{-1}$: 1755 (β-lactam, ester CO), 1720 (ketone CO).

NMR (CDCl$_3$) δ2.40 (6H, s,

), 3.00 (2H, m, —CH$_2$—CO), 3.50 (1H, d, J=1.5 Hz, H-3), 3.60 (2H, s, CH$_2$—COOPNB), 3.95 (1H, m, H-4), 5.30 (2H, s, COOC$\underline{H}_2$—Ar), 6.43 (1H, br, NH), 7.55 (2H, d, J=9.0 Hz

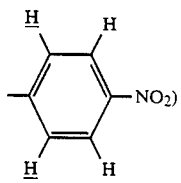

8.25 (2H, d, J=9.0 Hz

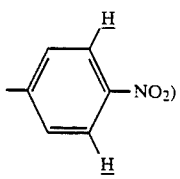

EXAMPLE 32

Production of
(3R,4R)-4-(3-diazo-3-p-nitrobenzyloxycarbonyl-2-oxo)-
propyl-3-dimethylamino-2-azetidinone [33]

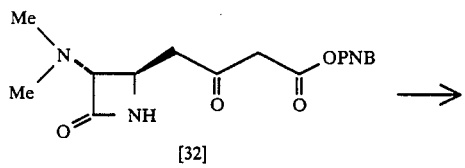

[32]

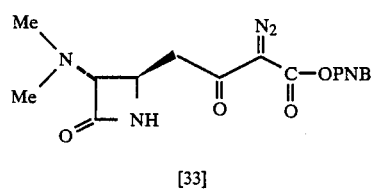

[33]

188 mg (0.57 mmol) of (3R,4R)-3-dimethylamino-4-(3-p-nitrobenzyloxycarbonyl-2-oxo)propyl-2-azetidinone [32] was dissolved in 5 ml of acetonitrile. The solution was cooled with ice, and 1.5 ml of acetonitrile containing 148 mg (0.75 mmol) of tosyl azide and 113 microliters (0.80 mmol) of triethylamine were added. The temperature of the reaction mixture was returned to room temperature, and reacted for 1 hour. The reaction mixture was poured into 100 ml of ethyl acetate, washed with an aqueous solution of sodium hydrogen carbonate and a saturated aqueous solution of sodium chloride. The extract was dried over anhydrous sodium sulfate. The solvent was evaporated. The residue was dissolved in a small amount of ethyl acetate, and adsorbed on a column of silica gel (15 g). The column was eluted with 110 ml of ethyl acetate/methanol (10/1) and 120 ml of ethyl acetate/methanol (5/1). Those fractions in the eluats which showed a UV absorption at an Rf of 0.08 in silica gel TLC developed with ethyl acetate were dried under reduced pressure to give 152 mg (yield 75%) of the captioned compound.

$\nu_{max}^{CHCl_3}$ cm$^{-1}$: 2195 (diazo), 1760 ($\beta$-lactam), 1720 (ketone CO).

NMR (CDCl$_3$) $\delta$2.39 (6H, s,

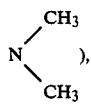

), 3.00 (1H, dd, J=9.0 and 17.5 Hz, C$\underline{H}$H—CO), 3.42 (1H, dd, J=4.0 and 17.5 Hz, CH$\underline{H}$—CO), 3.56 (1H, d, J=2.5 Hz, H-3), 4.00 (1H, ddd, J=2.5 and 4.0 and 9.0 Hz, H-4), 5.37 (2H, s, C$\underline{H}_2$Ar), 6.82 (1H, s, NH), 7.55 (2H, d, J=9.0 Hz,

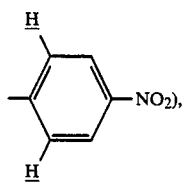

8.24 (2H, d, J=9.0 Hz,

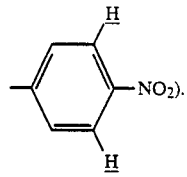

EXAMPLE 33

Production of p-nitrobenzyl
(2R,5R,6R)-6-dimethylamino-3,7-dioxo-1-azabicyclo[3.2.0]heptane-2-carboxylate [34]

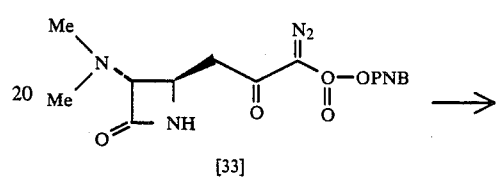

[33]

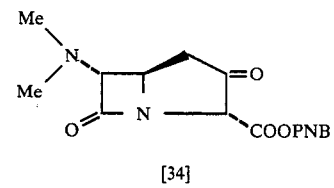

[34]

78 mg (0.22 mmol) of (3R,4R)-4-(3-diazo-3-p-nitrobenzyloxycarbonyl-2-oxo)propyl-3-dimethylamino-2-azetidinone [33] was dissolved in 15 ml of benzene, and 7 mg of rhodium acetate dimer was added. The mixture was refluxed for 1 hour. The reaction mixture was poured into 50 ml of ethyl acetate, washed with a saturated aqueous solution of sodium chloride and dried over anhydrous sodium sulfate. The solvent was evaporated to give 69 mg (yield 97%) of the captioned compound [34].

$\nu_{max}^{CHCl_3}$ cm$^{-1}$: 1765 $\beta$-lactam, ester, (ketone CO).

NMR (CDCl$_3$): $\delta$: 2.50 (1H, dd, J=18.5 and J=9.0 Hz, C$\underline{H}$H—CO), 2.70 (6H, s,

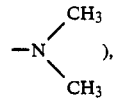

), 2.83 (1H, dd, J=18.5 and J=7.0 Hz, CH$\underline{H}$—CO), 4.0–4.35 (2H, m, H-5 and H-6), 4.80 (1H, s, H-2), 5.20 (1H, d, J=13.5 Hz, C$\underline{H}$H—Ar), 5.36 (1H, d, J=13.5 Hz, CH$\underline{H}$—Ar), 7.53 (2H, d, J=9.0 Hz 8.23 (2H, d, J=9.0 Hz,

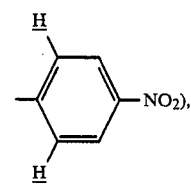

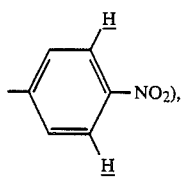

EXAMPLE 34

Production of p-nitrobenzyl (5R,6R)-3-(2-acetamidoethyl)thio-6-dimethylamino-7-oxo-1-azabicyclo[3.2.0]hept-2-ene-2-carboxylate [35]

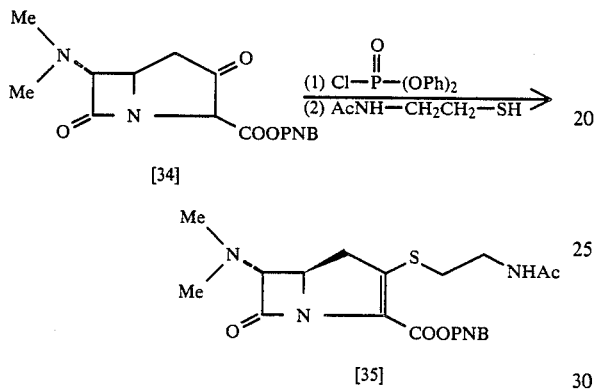

69 mg (0.21 mmol) of p-nitrobenzyl (2R,5R,6R)-6-dimethylamino-3,7-dioxo-1-azabicyclo[3.2.0]heptane-2-carboxylate [34] was dissolved in 1.5 ml of dimethylformamide. The solution was cooled to −35° C., and 45 microliters (0.32 mmol) of triethylamine and 58 microliters (0.28 mmol) of diphenylphosphoryl chloride was added, and the mixture was reacted at the above temperature for 30 minutes. The progress of the reaction was determined by the formation of a spot showing a UV absorption at an Rf of 0.46 in silica gel TLC developed with ethyl acetate, and the subsequent reaction was carried out. Specifically, 0.5 ml of a dimethylformamide solution of 54 microliters (0.38 mmol) of triethylamine and 46 mg (0.38 mmol) of N-acetylcysteamine was gradually added dropwise to the reaction mixture at −35° C. The reaction was carried out at the same temperature for 30 minutes. The reaction mixture was poured into 50 ml of ethyl acetate, and washed with 30 ml of 0.1M phosphate buffer (pH 8.9) and 20 ml of a saturated aqueous solution of sodium chloride. The washings were again extracted with ethyl acetate and washed with a saturated aqueous solution of sodium chloride. The extracts were combined, and dried over anhydrous sodium sulfate. The dried product was concentrated under reduced pressure to remove the solvent and 26 mg of crystals of the captioned compound were collected by filtration. The mother liquor was dried under reduced pressure, and dissolved in methylene chloride. The solution was adsorbed on a column of silica gel (7 g). The column was eluted with ethyl acetate, acetone and ethyl acetate/methanol (2/1). Those fractions in the eluates which had a UV absorption at an Rf of 0.15 in silca gel TLC developed with acetone were collected and dried under reduce pressure to give 49 mg (yield 83%) of the captioned compound.

$[\alpha]_D^{21}$ +57.4° (c=0.5, CHCl$_3$). $\lambda_{max}^{CH2Cl2}$ nm($\epsilon$): 325 (12500) 271 (12500).

$\nu_{max}^{ChCl3}$ cm$^{-1}$: 1775 ($\beta$-lactam CO) 1695 (ester CO) 1670 (amido CO) 1520, 1350 (nitro).

NMR (CDCl$_3$) $\delta$:2.00 (3H, s, COCH$_3$), 2.50 (6H, s,

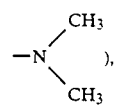

2.85–3.60 (6H, m, CH$_2\times$3), 3.93 (1H, d, J=3.0 Hz, H-6), 4.31 (1H, dt, J=3.0 and 9.0 Hz, H-5), 5.25 (1H, d, J=13.5 Hz, CH<u>H</u>—Ar), 5.53 (1H, d, J=13.5 Hz, C<u>H</u>H—Ar), 5.97 (1H, br, NH), 7.70 (2H, d, J=9.0 Hz,

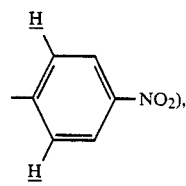

8.26 (2H, d, J=9.0 Hz,

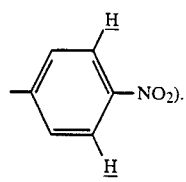

EXAMPLE 35

Production of (5R,6R)-3-(2-acetamidoethyl)thio-6-dimethylamino-7-oxo-1-azabicyclo[3.2.0]hept-2-ene-2-carboxylic acid [36]

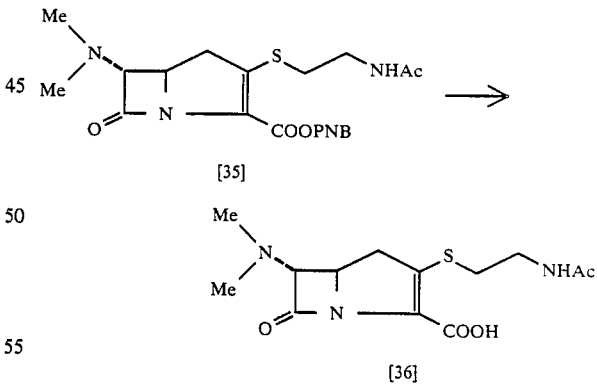

Forty milligrams (0.09 mmol) of p-nitrobenzyl (5R,6R)-3-(2-acetamidoethyl)thio-6-dimethylamino-7-oxo-1-azabicyclo[3.2.0]hept-2-ene-2-carboxylate [35] was dissolved in 5 ml of tetrahydrofuran and 2 ml of 0.01M phosphate buffer (pH 7.2), and catalystically reduced in the presence of 50 mg of platinum oxide at room temperature under 4 atmosphere for 3 hours. The reaction mixture was filtered, and concentrated under reduced pressure. The filtrate and the washing were combined, and sodium chloride was added to a concentration of 5%. The solution was adsorbed on a column of CHP-20 (20 ml). The column was eluted with deionized water. Those fractions in the eluates which showed a UV absorption at 307 nm were lyophilized to give 2 mg of the captioned compound.

UV $\lambda_{max}^{H2O}$ nm($\epsilon$)=307 (11500)

IR $\lambda_{max}^{KBr}$ cm$^{-1}$: 1740 ($\beta$-lactam CO) 1672 (amide CO), 1600 (carboxylate).

What we claim is:

1. A compound of the formula

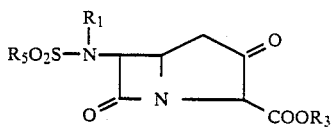

wherein
$R_1$ represents lower alkyl or lower haloalkyl,
$R_5$ is lower alkyl, and
$R_3$ represents a hydrogen atom or a carboxyl protecting group which can be easily split off.

* * * * *